United States Patent
Torii et al.

(10) Patent No.: US 11,633,717 B2
(45) Date of Patent: Apr. 25, 2023

(54) MEASUREMENT METHOD FOR PROPERTIES OF PARTICULATE ABSORBENT AGENT, AND PARTICULATE ABSORBENT AGENT

(71) Applicant: NIPPON SHOKUBAI CO., LTD., Osaka (JP)

(72) Inventors: Kazushi Torii, Hyogo (JP); Yuika Noda, Hyogo (JP); Daisuke Takagi, Hyogo (JP)

(73) Assignee: NIPPON SHOKUBAI CO., LTD., Osaka (JP)

(*) Notice: Subject to any disclaimer, the term of this patent is extended or adjusted under 35 U.S.C. 154(b) by 170 days.

(21) Appl. No.: 16/754,054

(22) PCT Filed: Oct. 12, 2018

(86) PCT No.: PCT/JP2018/038092
§ 371 (c)(1),
(2) Date: Apr. 6, 2020

(87) PCT Pub. No.: WO2019/074094
PCT Pub. Date: Apr. 18, 2019

(65) Prior Publication Data
US 2020/0324269 A1     Oct. 15, 2020

(30) Foreign Application Priority Data

Oct. 12, 2017 (JP) .............................. JP2017-198438
Dec. 8, 2017 (JP) .............................. JP2017-236491

(51) Int. Cl.
*B01J 20/26* (2006.01)
*B01J 20/28* (2006.01)
(Continued)

(52) U.S. Cl.
CPC ........... *B01J 20/261* (2013.01); *A61L 15/225* (2013.01); *A61L 15/24* (2013.01); *A61L 15/60* (2013.01);
(Continued)

(58) Field of Classification Search
None
See application file for complete search history.

(56) References Cited

U.S. PATENT DOCUMENTS

2004/0214946 A1   10/2004   Smith et al.
2005/0058810 A1   3/2005    Dodge et al.
(Continued)

FOREIGN PATENT DOCUMENTS

CN    1813033 A     8/2006
CN    104582833 A   4/2015
(Continued)

OTHER PUBLICATIONS

Office Action from corresponding Chinese Application No. 201880065382.2 dated Jan. 19, 2022.
(Continued)

*Primary Examiner* — Joseph D Anthony
(74) *Attorney, Agent, or Firm* — Harness Dickey & Pierce P.L.C.

(57) ABSTRACT

Provided are a water-absorbing resin having more excellent balance of fluid retention capacity, liquid permeability, and low dustiness and a novel measurement method which enables evaluation of excellent physical properties of the water-absorbing resin. A method for measuring an absorption speed of a particulate water-absorbing agent is a method including the step of applying pressure to a portion of a bottom surface of a measurement container (51) by use of a flat plate (52) in a state in which part or whole of the particulate water-absorbing agent (56) is fixed on the bottom
(Continued)

surface of the measurement container (51), the bottom surface being surrounded by a frame, introducing an aqueous solution through a liquid injection inlet (54) with which the flat plate (52) is equipped, and then measuring the amount of time elapsed until an end of absorption of the introduced aqueous solution by the particulate water-absorbing agent (56).

9 Claims, 6 Drawing Sheets

(51) Int. Cl.
*B01J 20/24* (2006.01)
*A61L 15/24* (2006.01)
*A61L 15/60* (2006.01)
*A61L 15/22* (2006.01)
*G01N 13/04* (2006.01)

(52) U.S. Cl.
CPC ......... *B01J 20/24* (2013.01); *B01J 20/28016* (2013.01); *G01N 13/04* (2013.01)

(56) References Cited

U.S. PATENT DOCUMENTS

| 2006/0282052 | A1 | 12/2006 | Saito et al. |
| 2007/0106013 | A1 | 5/2007 | Adachi et al. |
| 2011/0313113 | A1 | 12/2011 | Sakamoto et al. |
| 2012/0258851 | A1 | 10/2012 | Nakatsuru et al. |
| 2012/0277711 | A1* | 11/2012 | Kim ............... A61F 13/535 604/374 |
| 2013/0026412 | A1 | 1/2013 | Machida et al. |
| 2013/0101851 | A1 | 4/2013 | Takaai et al. |
| 2014/0296465 | A1 | 10/2014 | Sakamoto et al. |
| 2015/0217270 | A1 | 8/2015 | Ueda et al. |
| 2015/0246992 | A1 | 9/2015 | Ueda et al. |
| 2015/0259494 | A1 | 9/2015 | Takaai et al. |
| 2016/0199529 | A1 | 7/2016 | Torii et al. |
| 2016/0207226 | A1 | 7/2016 | Torii et al. |
| 2016/0332141 | A1 | 11/2016 | Machida et al. |
| 2017/0014801 | A1 | 1/2017 | Ikeuchi et al. |
| 2017/0216817 | A1 | 8/2017 | Torii et al. |
| 2018/0001300 | A1 | 1/2018 | Nakatsuru et al. |
| 2018/0094131 | A1 | 4/2018 | Tanaka et al. |
| 2019/0091660 | A1 | 3/2019 | Ueda et al. |
| 2019/0275192 | A1 | 9/2019 | Torii et al. |

FOREIGN PATENT DOCUMENTS

| CN | 106715543 A | 5/2017 |
| CN | 107107027 A | 8/2017 |
| EP | 3156427 A1 | 4/2017 |
| EP | 3202823 A1 | 8/2017 |
| EP | 3278873 A1 | 2/2018 |
| EP | 3586957 A1 | 1/2020 |
| JP | H0570762 A | 3/1993 |
| JP | 2606988 B2 | 5/1997 |
| JP | 200598956 A | 4/2005 |
| JP | 2005334616 A | 12/2005 |
| JP | 2016209111 A | 12/2016 |
| WO | 2011126079 A1 | 10/2011 |
| WO | 2014046106 A1 | 3/2014 |
| WO | 2015030129 A1 | 3/2015 |
| WO | 2015030130 A1 | 3/2015 |
| WO | 2015129917 A1 | 9/2015 |
| WO | 2016158976 A1 | 10/2016 |

OTHER PUBLICATIONS

Partial Supplementary European Search Report from corresponding EP Application No. 18865632.6 dated Jun. 8, 2021.
International Preliminary Report on Patentability for corresponding PCT Application No. PCT/JP2018/038092 dated Apr. 23, 2020.
International Search Report for corresponding PCT Application No. PCT/JP2018/038092 dated Jan. 8, 2019.
Extended European Search Report from corresponding European Application No. 188656326 dated Nov. 17, 2021.

* cited by examiner

MEASUREMENT METHOD FOR PROPERTIES OF PARTICULATE ABSORBENT AGENT, AND PARTICULATE ABSORBENT AGENT

TECHNICAL FIELD

The present invention relates to a method for measuring physical properties of a particulate water-absorbing agent. The present invention also relates to a particulate water-absorbing agent having high absorption performance.

BACKGROUND ART

Water-absorbing resin (super absorbent polymer or SAP) is a water-swellable, water-insoluble polymer gelling agent. Water-absorbing resin is used in various applications including use in sanitary materials such as disposable diapers, sanitary napkins, and adult incontinence products, agricultural and horticultural water retaining agents for soil, and industrial waterproofing agents. Many types of monomers and hydrophilic polymers have been proposed as raw materials for such water-absorbing resin. From the viewpoint of performance and cost, a polyacrylic acid (salt)-based water-absorbing resin containing an acrylic acid and/or a salt thereof (hereinafter referred to as "acrylic acid (salt)") as a monomer(s) is most often used as such water-absorbing resin.

Disposable diapers, which are one of the main applications of water-absorbing resin, have undergone advances in performance. Along with these advances have come requirements for the water-absorbing resin to have a large number of functions (physical properties). Specific examples of the physical properties of the water-absorbing resin include not only merely a high fluid retention capacity but also gel strength, water-soluble content, water absorption speed, fluid retention capacity under pressure, liquid permeability, particle size distribution, urine resistance, antibacterial property, impact resistance (damage resistance), powder fluidity, deodorizing property, anti-coloring property (whiteness), low dustiness, and the like. For example, Patent Literature 1 (International Publication No. WO 2011/126079) discloses a water-absorbing resin powder in which both liquid permeability and water absorption speed are achieved, as well as a method of producing the water-absorbing resin powder. Patent Literature 2 (International Publication No. WO 2015/030129) discloses improving the fluid retention capacity under pressure of a water-absorbing resin powder. Specifically, in a gel-crushing step (a production step of the water-absorbing resin powder), hydrogel is further crushed with use of a specific form of device. Patent Literature 3 (International Publication No. WO 2015/030130) discloses improving liquid permeability of a water-absorbing resin powder. Specifically, in a gel-crushing step (a production step of the water-absorbing resin powder), hydrogel is further crushed in a kneading manner with use of a specific form of device. Patent Literature 4 (International Publication No. WO 2015/129917) discloses a water-absorbing agent having reduced re-wet during actual use in an absorbent article, the water-absorbing agent being defined by gel capillary absorption (GCA), etc.

CITATION LIST

Patent Literatures

[Patent Literature 1]
International Publication No. WO 2011/126079
[Patent Literature 2]
International Publication No. WO 2015/030129
[Patent Literature 3]
International Publication No. WO 2015/030130
[Patent Literature 4]
International Publication No. WO 2015/129917

SUMMARY OF INVENTION

Technical Problem

However, the water-absorbing resins disclosed in the Patent Literatures listed above cannot achieve a sufficient function, and thus, there is a demand for a water-absorbing resin having more excellent balance of fluid retention capacity, liquid permeability, and low dustiness. Moreover, various methods for measuring physical properties of a water-absorbing resin have conventionally been proposed. For further performance improvement, there is a situation that requires the development of a novel evaluation method.

In view of this, it is an object of the present invention to provide a water-absorbing resin excellent in the above-described physical properties and a measurement method which enables evaluation of excellent physical properties of the water-absorbing resin.

Solution to Problem

The inventors of the present invention have revealed, through diligent study, that the measurement method described below can achieve the above object. That is, (Item 1) A method for measuring an absorption speed of a particulate water-absorbing agent, including the step of: applying pressure to a portion of a bottom surface of a measurement container by use of a flat plate in a state in which part or whole of said particulate water-absorbing agent is fixed on the bottom surface of the measurement container, the bottom surface being surrounded by a frame, introducing an aqueous solution through an injection inlet with which the flat plate is equipped, and then measuring the amount of time elapsed until an end of absorption of the introduced aqueous solution by said particulate water-absorbing agent.

(Item 2) A method for measuring an absorption speed of a particulate water-absorbing agent, including the steps of:
applying pressure to a portion of a bottom surface of a measurement container by use of a flat plate in a state in which part or whole of said particulate water-absorbing agent is fixed on the bottom surface of the measurement container, the bottom surface being surrounded by a frame, introducing an aqueous solution through an injection inlet with which the flat plate is equipped, so that the introduced aqueous solution is absorbed by said particulate water-absorbing agent; and removing the flat plate after an elapse of a predetermined period of time since the aqueous solution has been introduced, placing a member capable of absorbing the aqueous solution on a top of said particulate water-absorbing agent, applying pressure for a predetermined time period, and measuring a mass of a portion of the aqueous solution, the portion being a portion absorbed by the member, to measure a re-wet of a liquid from said particulate water-absorbing agent.

(Item 3) A particulate water-absorbing agent having the following physical properties (1) and (2):

(1) a centrifuge retention capacity (CRC) of 30 g/g to 50 g/g; and (2) an absorbent performance index (API) of 150 or less, the absorbent performance index (API) being expressed by the following formula:

Absorbent performance index (API)=First absorption time [sec]×Second absorption time [sec]×Third absorption time [sec]×Re-wet [g]/1000.

(Item 4) A particulate water-absorbing agent having the following physical properties (1) and (2):

(1) a centrifuge retention capacity (CRC) of 30 g/g to 50 g/g; and (2) a new absorbent performance index (nAPI) of 240 or less, the new absorbent performance index (nAPI) being expressed by the following formula:

New absorbent performance index (nAPI)=Second absorption time [sec]×Third absorption time [sec]×Re-wet [g]/10.

In the present invention, it is intended that one or more of the characteristics above can be provided not only in combination disclosed clearly above but also in further combinations. Further embodiments and advantages of the present invention will be recognized by a person skilled in the art through, as necessary, reading and understanding the detailed description below.

Advantageous Effects of Invention

The present invention allows physical properties required for a particulate water-absorbing agent to be measured by a method which is easier than the conventional measurement method. Further, it is possible to provide a particulate water-absorbing agent that has more excellent balance of fluid retention capacity, liquid permeability, and low dustiness and exhibits more excellent performance in an absorbent body than the conventional particulate water-absorbing agent.

DESCRIPTION OF EMBODIMENTS

Figure 1:
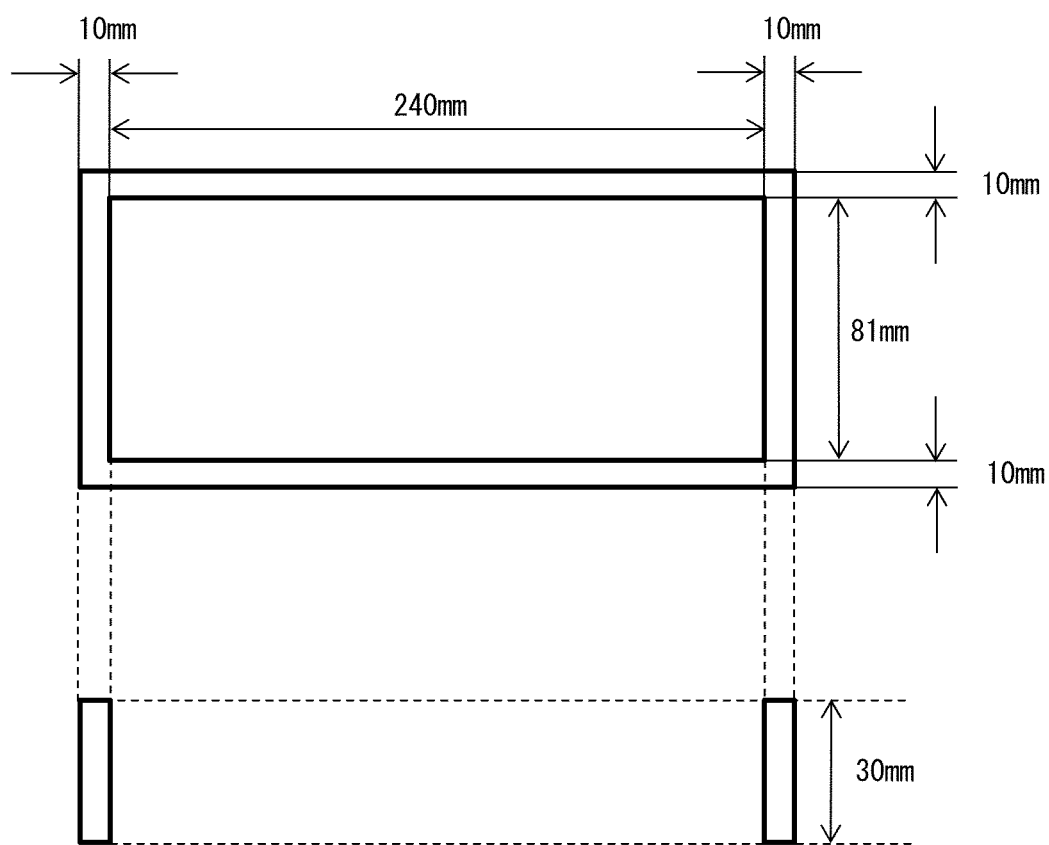
FIG. 1 is a plan view illustrating an example of a measurement container, of a measurement device used in a measurement method according to the present invention, having a bottom surface surrounded by a frame.

The following description will discuss the best mode of the present invention. Throughout the present specification, any expression in a singular form should be understood to encompass the concept of its plural form unless particularly mentioned otherwise. Therefore, the article specifying a single form (e.g., "a", "an", "the") should be understood to encompass the concept of its plural form unless particularly mentioned otherwise. In addition, any term used in the present specification should be understood as ordinarily used in this technical field unless particularly mentioned otherwise. Therefore, unless defined otherwise, all of the technical terms and scientific terms used in the present specification mean as generally understood by a person skilled in the technical field to which the present invention belongs. If there is any conflict in meaning, the present specification (including the definitions) take priority.

[1] Definitions of Terms (1-1) "Water-Absorbing Resin"

The term "water-absorbing resin" as used in the present invention refers to a water-swellable, water-insoluble polymer gelling agent that satisfies the following physical properties. Specifically, the term "water-absorbing resin" refers to a polymer gelling agent that satisfies the following physical properties: CRC (centrifuge retention capacity) defined in ERT 441.2-02 as "water-swelling property" is 5 g/g or more, and Ext (extractable) defined in ERT470.2-02 as "water-insolubility" is 50 mass % or less.

The water-absorbing resin can be designed as appropriate according to its purpose of use, and is not limited to a particular design. The water-absorbing resin is preferably a hydrophilic crosslinked polymer that has been obtained by crosslinking and polymerizing unsaturated monomers each of which has a carboxyl group. The water-absorbing resin is not limited to a form in which the water-absorbing resin is wholly (that is, 100 mass %) a polymer, and can be a water-absorbing resin composition containing an additive and the like within a range in which the above-described physical properties (CRC and Ext) are satisfied.

The water-absorbing resin as used in the present invention may refer to not only an end product but also an intermediate produced during a process of producing the water-absorbing resin (e.g. a crosslinked hydrogel polymer after polymerization, a dried polymer after drying, a water-absorbing resin powder before surface crosslinking, or the like). In addition, the water-absorbing resin as used in the present invention and the water-absorbing resin composition described above will also be collectively referred to as "water-absorbing resin". Examples of forms of the water-absorbing resin encompass a sheet form, a fiber form, a film form, a particulate form, and a gel form. The water-absorbing resin of the present invention is preferably a particulate water-absorbing resin.

(1-2) "Particulate Water-Absorbing Agent"

The term "water-absorbing agent" as used in the present invention means a gelling agent which contains a water-absorbing resin as a main component and absorbs a water-based liquid. The term "particulate water-absorbing agent"

as used in the present invention means a water-absorbing agent in the form of particles or powder, and the term "particulate water-absorbing agent" is used to refer to a single particle of the water-absorbing agent or an aggregate of a plurality of particles of the water-absorbing agent. The term "particulate" means having the form of particles. A particle is a small grain-shaped solid or liquid object with a measurable size (according to the Glossary of Technical Terms in Japanese Industrial Standards, fourth edition, page 2002). Note that the particulate water-absorbing agent may be simply referred to as "water-absorbing agent".

Note that the "water-based liquid" is not limited to water. Examples of the water-based liquid encompass water-based liquids such as urine, blood, sweat, feces, waste fluid, moisture, vapor, ice, a mixture of water and an organic solvent and/or an inorganic solvent, rain water, and ground water. The water-based liquid may be any liquid that contains water. Preferable examples of the water-based liquid encompass urine, menstrual blood, sweat, and other body fluids.

The particulate water-absorbing agent in accordance with the present invention is suitably used in a hygienic material for absorbing a water-based liquid. A water-absorbing resin serving as a polymer is contained as a main component in a particulate water-absorbing agent. Specifically, the particulate water-absorbing agent contains the water-absorbing resin in an amount of preferably 60 mass % to 100 mass %, 70 mass % to 100 mass %, 80 mass % to 100 mass %, or 90 mass % to 100 mass %. The particulate water-absorbing agent optionally further contains, as a non-polymer, water and/or an additive (such as inorganic fine particles and polyvalent metal cations). A suitable moisture content is 0.2 mass % to 30 mass %. The scope of the particulate water-absorbing agent also encompasses a water-absorbing resin composition in which these components are integrated.

The particulate water-absorbing agent contains the water-absorbing resin in an amount up to approximately 100 mass %, more preferably 99 mass %, further preferably 97 mass %, particularly preferably 95 mass % or 90 mass %. Preferably, the water-absorbing agent further contains a component(s) in an amount of 0 mass % to 10 mass % other than the water-absorbing resin. The water-absorbing agent particularly preferably further contains water and/or an additive (inorganic fine particles or polyvalent metal cations) described later.

Examples of the water-absorbing resin to be contained as a main component in the particulate water-absorbing agent encompass a polyacrylic acid (salt)-based resin, a polysulfonic acid (salt)-based resin, a maleic anhydride (salt)-based resin, a polyacrylamide-based resin, a polyvinyl alcohol-based resin, a polyethylene oxide-based resin, a polyaspartic acid (salt)-based resin, a polyglutamic acid (salt)-based resin, a polyalginic acid (salt)-based resin, a starch-based resin, and a cellulose-based resin. The water-absorbing resin is preferably a polyacrylic acid (salt)-based resin.

(1-3) "Polyacrylic Acid (Salt)"

The term "polyacrylic acid (salt)" as used in the present invention refers to polyacrylic acid and/or a salt thereof, and refers to a polymer that contains, as a main component, a repeating unit of acrylic acid and/or a salt thereof (hereinafter referred to as "acrylic acid (salt)") and that contains a graft component as an optional component. The polyacrylic acid can be obtained by hydrolysis of polyacrylamide, polyacrylonitrile, and the like. The polyacrylic acid is preferably obtained by polymerization of an acrylic acid (salt).

The term "main component" means that the acrylic acid (salt) is used (contained) in an amount of ordinarily 50 mol % to 100 mol %, preferably of 70 mol % to 100 mol %, more preferably of 90 mol % to 100 mol %, and even more preferably of substantially 100 mol %, relative to a total amount of monomers for use in polymerization (excluding an internal crosslinking agent).

(1-4) "EDANA" and "ERT"

The term "EDANA" is an acronym for the European Disposables and Nonwovens Associations. The term "ERT" is an acronym for EDANA Recommended Test Methods, which are European standard (de facto international standard) measuring methods for water-absorbing resin. For the present invention, physical properties of water-absorbing resin are measured in conformity with the ERT master copy (2002 revised version; known literature) unless otherwise specified.

(1-4-1) "CRC" (ERT 441.2-02)

The term "CRC" is an acronym for "centrifuge retention capacity", and means a fluid retention capacity without pressure (hereinafter referred to also as "fluid retention capacity") of a particulate water-absorbing agent or of a water-absorbing resin. Specifically, the CRC refers to a fluid retention capacity (unit: g/g) measured after 0.2 g of a particulate water-absorbing agent or a water-absorbing resin contained in a nonwoven fabric bag is immersed in a large excess of a 0.90 mass % aqueous sodium chloride solution for 30 minutes so as to be allowed to freely swell, and then the water-absorbing resin is drained in a centrifuge (250 G).

Note that the CRC of a crosslinked hydrogel polymer (hereinafter referred to as "gel CRC") was measured while the weight of a sample and the free swelling period are changed to 0.4 g and 24 hours, respectively. In calculation of numerical values in the measurement, the mass of a resin solid content of a crosslinked hydrogel polymer was used as the mass of the water-absorbing resin. In a case where each side of the crosslinked hydrogel polymer had a size of 5 mm or more, the crosslinked hydrogel polymer was, before the measurement, cut with use of scissors or the like so that the side has a size of 1 mm or less.

(1-4-2) "AAP" (ERT 442.2-02)

The term "AAP" is an acronym for "absorption against pressure", and means a fluid retention capacity under pressure of a particulate water-absorbing agent or a water-absorbing resin.

Specifically, "AAP" refers to a fluid retention capacity (unit: g/g) measured after 0.9 g of particulate water-absorbing agent or water-absorbing resin has been swollen in a large excess of a 0.90 mass % aqueous sodium chloride solution for 1 hour under a load of 2.06 kPa (21 g/cm$^2$, 0.3 psi). Note that in some cases the measurement may be carried out under a load of 4.83 kPa (49 g/cm$^2$, 0.7 psi). Note that ERT 442.2-02 uses the term "Absorption Under Pressure", which refers to substantially the same thing as "Absorption Against Pressure".

(1-4-3) "PSD" (ERT 420.2-02)

The term "PSD" is an acronym for "particle size distribution", and means a particle size distribution of a particulate water-absorbing agent or a water-absorbing resin. The particle size distribution is measured by sieve classification.

Note that the mass average particle diameter (D50) and the logarithmic standard deviation (σ$\zeta$) of a particle size distribution are measured according to a method similar to "(3) Mass-Average Particle Diameter (D50) and Logarithmic Standard Deviation (σ$\zeta$) of Particle Diameter Distribution", which is a method disclosed in U.S. Pat. No. 7,638,570.

(1-4-4) "Moisture Content" (ERT 430.2-02)

The term "moisture content" means a moisture content of a particulate water-absorbing agent or a water-absorbing resin. Specifically, a "moisture content" refers to a value (unit: mass %) calculated from a drying loss from drying 4.0 g of a particulate water-absorbing agent or a water-absorbing resin at 105° C. for 3 hours. Note that in some cases, measurement may be carried out while the amount of the particulate water-absorbing agent or the water-absorbing resin and the drying temperature are changed to 1.0 g and 180° C., respectively.

(1-4-5) "Ext" (ERT 470.2-02)

The term "Ext" is an abbreviation for "Extractables", and means a water-soluble content (water-soluble component amount) of a particulate water-absorbing agent or a water-absorbing resin. Specifically, the "Ext" refers to the amount (unit: mass %) of a polymer dissolved in an aqueous solution after adding 1.0 g of particulate water-absorbing agent or water-absorbing resin to 200 ml of a 0.90 mass % aqueous sodium chloride solution and stirring the resulting mixture at 500 rpm for 16 hours. The amount of the dissolved polymer is measured by pH titration.

(1-5) "DRC"

The term "DRC" is an abbreviation for "Dunk Retention Capacity" and means a fluid retention capacity without pressure of a particulate water-absorbing agent or a water-absorbing resin. Specifically, the "DRC" refers to a fluid retention capacity (unit: g/g) after, as in the case of measurement of the AAP, 1.0 g of particulate water-absorbing agent or water-absorbing resin is dispersed uniformly in a cylindrical cell having a mesh at a bottom surface thereof and then a resulting product is allowed to be in contact with a 0.90 mass % aqueous sodium chloride solution for 5 minutes so as to freely swell. A measuring method will be described in detail in Examples. Note that since the free swelling period is 5 minutes, the "DRC" is denoted as "DRC5 min".

(1-6-1) "General Index of DRC"

"General index of DRC" is a parameter defined by the following Formula 2.

$$\text{General index of DRC} = (K - \text{DRC5 min})/(D50/1000) \quad \text{Formula 2}$$

In Formula 2, K is any constant. A proper value of K can be decided by producing various particulate water-absorbing agents, measuring DRC5 min (unit: g/g) and D50 (unit: μm), and determining whether or not a preferable particulate water-absorbing agent(s) was/were obtained. The general index of DRC is useful as an index for determining a particulate water-absorbing agent having preferable physical properties.

(1-6-2) "Index of DRC"

"Index of DRC" is a parameter defined by the following Formula 1.

$$\text{Index of DRC} = (49 - \text{DRC5 min})/(D50/1000) \quad \text{Formula 1}$$

The index of DRC corresponds to a case where the value of K in the general index of DRC is 49. As in the case of the general index of DRC, the index of DRC is useful as an index for determining a particulate water-absorbing agent having preferable physical properties.

(1-7) "GPR"

The term "GPR" is an abbreviation for "Gel Permeation Rate" and refers to a rate (unit: g/min) of flow of a liquid passing through in-between particles of a swollen gel which was obtained by allowing a particulate water-absorbing agent or a water-absorbing resin to swell under load. The gel permeation rate (GPR) is preferably 25 g/min or more, more preferably 50 g/min or more, and most preferably 100 g/min or more. An upper limit of the gel permeation rate (GPR) is not particularly limited but is preferably 1000 g/min or less. A measuring method will be described in detail in Examples.

(1-8) "Non-Uniformly Pulverized Shape"

The term "non-uniformly pulverized shape" refers to a shape of a crushed substance obtained by crushing a crosslinked hydrogel polymer or a dried polymer of such a crosslinked hydrogel polymer (preferably a dried polymer of such a crosslinked hydrogel polymer) during or after polymerization, and refers to a non-uniform, pulverized shape. The crushed substance having a non-uniformly pulverized shape is preferably obtained by aqueous solution polymerization. In contrast, in a case where a pulverizing step is not carried out, typically in a case where, for example, reversed phase suspension polymerization is carried out or droplet polymerization is carried out by spraying polymerizable monomers into a liquid phase, a resulting crosslinked hydrogel polymer has a spherical shape, and a granulated material of spherical particles does not have a non-uniformly pulverized shape.

(1-9) "Moisture Absorption Fluidity"

The term "moisture absorption fluidity" refers to an index for evaluating blocking, caking, or powder fluidity of a particulate water-absorbing agent or a water-absorbing resin after the particulate water-absorbing agent or the water-absorbing resin was left to sit for 1 hour in an atmosphere at an air temperature of 25° C. and at a relative humidity of 90% RH. The "moisture absorption fluidity" is also denoted as "moisture absorption fluidity (B.R.)" or "moisture adsorption blocking ratio". A method of calculating the moisture absorption fluidity will be described in detail in Examples, but is briefly described as below.

The moisture absorption fluidity is calculated as follows. A particulate water-absorbing agent or a water-absorbing resin is classified with use of a sieve. Then, the mass (W1) (unit: g) of the particulate water-absorbing agent or water-absorbing resin remaining on the sieve and the mass (W2) (unit: g) of the particulate water-absorbing agent or water-absorbing resin which has passed through the sieve are measured. Then, the moisture absorption fluidity is calculated according to the following Formula 3.

$$\text{Moisture absorption fluidity } (B.R.) = \{W1/(W1+W2)\} \times 100 \quad \text{Formula 3}$$

(1-10) "Moisture Absorption Fluidity Improving Agent"

The term "moisture absorption fluidity improving agent" refers to a compound or a composition which increases the moisture absorption fluidity of a particulate water-absorbing agent or a water-absorbing resin. Note that a smaller value in the moisture absorption fluidity (B.R.) means superior moisture absorption fluidity.

As the moisture absorption fluidity improving agent as used in the present invention, silicon dioxide, hydrotalcite, phosphate, and aluminum salt can be used. More specifically, a multicomponent metal compound having a hydrotalcite structure and containing divalent and trivalent metal cations (two kinds of metal cations) and a hydroxyl group, and water-insoluble metal phosphate containing an anion of a phosphoric acid and a divalent or trivalent metal cation can be used.

(1-11) "Degradable Soluble Content"

The term "degradable soluble content" refers to a water-soluble content measured by the method of measuring "Ext" described in the section (1-4-5) above, in a case where the 0.90 mass % aqueous sodium chloride solution is changed to a 0.90 mass % aqueous sodium chloride solution (degradation test liquid) which is mixed with L-ascorbic acid, and the 0.90 mass % aqueous sodium chloride solution is allowed to stand still at 60° C. for 2 hours and is then stirred for 1 hour.

(1-12) "Gel-Grinding Energy" (GGE)

The term "gel-grinding energy" refers to mechanical energy per unit mass (unit mass of a crosslinked hydrogel polymer), the mechanical energy being necessary for a gel-crushing device to gel-crush a crosslinked hydrogel polymer. The "gel-grinding energy" does not include energy with which to heat or cool a jacket, or energy of water and/or steam to be introduced. Note that the "gel-grinding energy" is abbreviated as "GGE". In a case where the gel-crushing device is driven by a three-phase alternating current power, the GGE is calculated based on the following Formula 4.

$$\text{GGE (J/g)} = \{\sqrt{3} \times \text{voltage} \times \text{electric current} \times \text{power factor} \times \text{motor efficiency}\} / \{\text{mass of crosslinked hydrogel polymer introduced into gel crusher per second}\} \quad \text{Formula 4}$$

The "power factor" and the "motor efficiency" are each a value which is unique to the gel-crushing device and changes depending on, for example, an operation condition of the gel-crushing device and which ranges from 0 to 1. These values can be known by, for example, making inquiries to a manufacturer of the device or the like. In a case where the gel-crushing device is driven by a single-phase alternating current power, GGE can be calculated by replacing "$\sqrt{3}$" with "1" in Formula 4. Note that a unit of a voltage is (V), a unit of an electric current is (A), and a unit of mass of a crosslinked hydrogel polymer is (g/s). GGE is measured by the method disclosed in International Publication No. WO 2011/126079. Since the mechanical energy to be applied to the crosslinked hydrogel polymer is important, the gel-grinding energy is preferably calculated by subtracting an electric current value of the gel-crushing device during idling from an electric current value of the gel-crushing device during gel-crushing. In a case where gel-crushing is carried out with use of a plurality of gel-crushing devices, in particular, a sum of electric current values of the plurality of gel-crushing devices during idling is large. It is therefore suitable to calculate the gel-grinding energy by subtracting the electric current values of the plurality of gel-crushing devices during idling from current values of the plurality of gel-crushing devices during gel-crushing. In this case, the gel-grinding energy is calculated by the following Formula 5. Note that this gel-grinding energy is denoted as GGE (2) to be distinguished from the GGE described earlier.

$$\text{GGE(2) (J/g)} = \{\sqrt{3} \times \text{voltage} \times (\text{electric current during gel-crushing} - \text{electric current during idling}) \times \text{power factor} \times \text{motor efficiency}\} / \{\text{mass of crosslinked hydrogel polymer introduced into gel crusher per second}\} \quad \text{Formula 5}$$

The "power factor" and the "motor efficiency" during gel-crushing are applied to the GGE (2). Since the electric current value during idling is small, the values of the power factor and the motor efficiency during idling are defined approximately as in Formula 5. For example, in a case where an amount of the crosslinked hydrogel polymer to be continuously fed by a quantitative feeder is [t/hr], the "mass of crosslinked hydrogel polymer to be introduced into gel crusher per second" in each of Formulas 4 and 5 refers to a value obtained by converting [t/hr] into [g/s].

(1-13) "Surface Tension"

The term "surface tension" refers to a surface tension that indicates, in a per-unit-area basis, work (free energy) necessary for increasing a surface area of a solid or a liquid. The term "surface tension" as used in the present invention refers to a surface tension of an aqueous solution obtained by dispersing a particulate water-absorbing agent or a water-absorbing resin in a 0.90 mass % aqueous sodium chloride solution. A measuring method will be described in detail in Examples.

(1-14) "Bulk Specific Gravity"

The term "bulk specific gravity" refers to a specific gravity when a container having a certain volume capacity is filled with a powder and the volume capacity is regarded as a volume. A measuring method will be described in detail in Examples.

(1-15) "DAP"

"DAP", which is an abbreviation for diffusing absorbency under pressure, is a physical property value for evaluating the absorption amount of a water-absorbing resin and takes account of diffusion ability of a water-based liquid in a case where the water-absorbing resin has a high basis weight and is in a state where particles of the water-absorbing resin are in close contact due to an external force. The diffusing absorbency under pressure is calculated from a measured value obtained by measurement under certain conditions after an elapse of a certain period of time (60 minutes or 10 minutes) from a start of adsorption. Note that a value after an elapse of 10 minutes (value after 10 minutes) is denoted as "DAP10min". A measuring method will be described in detail in Examples.

(1-16) "Internal Gas Bubble Ratio"

The term "internal gas bubble ratio" refers to a value calculated by the following Formula. A measuring method will be described in detail in Examples.

$$\text{Internal gas bubble ratio [\%]} = \{(\text{true density [g/cm}^3\text{]} - \text{apparent density [g/cm}^3\text{]})/\text{true density [g/cm}^3\text{]}\} \times 100$$

The term "true density" as used in the present invention means a density (unit: [g/cm$^3$]) of polyacrylic acid (salt)-based water-absorbing resin which was dried sufficiently (so as to have a moisture content of preferably less than 1 mass %, more preferably less than 0.5 mass %, and particularly preferably less than 0.1 mass %), the density being fixedly decided by a chemical composition (for example, repeating units of a polymer, minute raw materials such as a crosslinking agent, and graft component used optionally). Therefore, the true density of polyacrylic acid (salt)-based water-absorbing resin exhibited is substantially constant, although the true density may slightly vary due to its neutralization rate, the type of the salt of the neutralization (for example, sodium polyacrylate having a neutralization rate of 75 mol %), or the amount and type of the minute raw material.

In contrast, the term "apparent density" as used in the present invention means a density (unit: [g/cm$^3$]) in view of spaces present in particles of a polyacrylic acid (salt)-based water-absorbing resin (hereinafter such spaces will also be referred to as "internal gas bubbles" or "closed cells"). For example, a water-absorbing resin, which has been obtained by foaming polymerization or has been subjected to a granulation step, has internal voids (spaces; internal gas bubbles; closed cells; closed pores) that are not connected to the outside. Therefore, in a case where the density of a water-absorbing resin is measured by dry density measurement, introduced gas cannot enter the closed pores. This causes a measured density to be an apparent density which is obtained from the volume including those of the closed pores (e.g., closed cells). Modern Superabsorbent polymer Technology (1998) (p. 197-199) discloses that the apparent density of a water-absorbing resin having particles that have been subjected to 40 to 60 mesh-cut is measured by a wet measurement method that uses methanol. However, the apparent density of the present invention is characterized in that the dry measurement is carried out for all particle sizes of a polyacrylic acid (salt)-based water-absorbing resin. The inventors of the present invention found that the internal gas bubble ratio specified by such apparent density has an important influence on improvement in physical properties of a water-absorbing resin.

The density (true density and apparent density) of a water-absorbing resin can be accurately measured by the dry density measurement in which a certain gas is used. A measurement principle of the dry density measurement for a solid is well known in an isovolumetric swelling method. The dry density measurement is a method in which the volume of a solid is determined by use of a specific gas. Specifically, assuming that the volume of a sample chamber, VCELL, and the volume of an expansion chamber, VEXP, are known, the volume of the sample, VSAMP, can be determined by measuring pressures (gage pressures) P1g and P2g. The density of the sample can be determined by dividing a mass of the sample, which is separately measured, by the volume of the sample (see the web page of Shimadzu Corporation; http://www.shimadzu.co.jp/powder/lecture/middle/m04.html).

The true density is fixedly decided by a chemical composition (mainly, repeating units of a polymer). Thus, a known value may be used as the true density. If there is no known value for the true density of a water-absorbing resin because the true density varies slightly due to, for example, a minute raw material of the water-absorbing resin, the true density may be determined by a method described later (method described in Examples). A water-absorbing resin having virtually no closed cells can be obtained by pulverizing a water-absorbing resin to break closed cells inside the water-absorbing resin or to turn the closed cells inside the water-absorbing resin into open cells. Thus, the density of a water-absorbing resin after pulverization can be regarded as true density. Note that the "open cells" means cells communicating with an environment outside a water-absorbing resin and are not measured into the volume of a water-absorbing resin in the dry density measurement. Thus, the closed cells and the open cells can be easily distinguished from each other by the dry density measurement.

(1-17) Others

In the present specification, any range of "X to Y" means "X or more and Y or less". Further, the unit of mass "t (ton)" means "metric ton". Further, " . . . acid (salt)" means " . . . acid and/or salt thereof", and "(meth)acrylic" means "acrylic and/or methacrylic". For convenience, "liter" may be referred to as "l" or "L", and "mass %" may be referred to as "wt %". Furthermore, in a case where a trace component is measured, a value equal to or less than a detection limit is indicated as N.D. (Non Detected).

[2] Method for Measuring Physical Properties of Particulate Water-Absorbing Agent The following description will discuss a method for measuring physical properties of a particulate water-absorbing agent in accordance with the present invention ((2-1) to (2-6)). Note that the measurement is carried out in an atmosphere at room temperature (20° C. to 25° C.) and at a relative humidity of 40% RH to 60% RH (preferably 45% RH to 55% RH).

(2-1) Measurement Device

A measurement device used in the present invention is a measurement container that has a bottom surface surrounded by a frame (Note that the frame is not necessarily a fixed frame, provided that it can prevent a liquid from leaking out of the measurement device. In the present invention, a mechanism capable of preventing a liquid from leaking out of the measurement device is defined as "frame".).

The material of the container is not limited to any specific material, but is preferably a resin (plastic).

The height of the frame surrounding the bottom surface is not limited to any specific height, but is preferably 1 cm or more, more preferably 2 cm or more, and most preferably 3 cm or more. An upper limit of the height of the frame is not limited to any specific value, but is ordinarily preferably 5 cm or less. A frame having a low height may cause leakage of the liquid, whereas a frame having an excessively high height is difficult to handle. The frame is preferably vertical to the bottom surface. Note that the thickness of the frame is not limited to any specific thickness, but is preferably approximately 0.5 cm to 1 cm.

The bottom surface of the measurement device may be secured or can alternatively be a bottom surface that is formed by an attached tape or the like. The top of the measurement device is preferably open.

The shape of the container is not limited to any specific shape, but is preferably rectangular. If the container is rectangular, the aspect ratio when the measurement container is viewed from above is preferably 1:1.5 to 1:10, more preferably 1:2 to 1:8, and most preferably 1:2.5 to 1:5. Further, if the container is not rectangular, a ratio between a major axis and a minor axis obtained by elliptic approximation is regarded as the aspect ratio. Note that calculation of the above-described aspect ratio is performed based on a bottom surface part surrounded by the frame.

The size of the container is not limited to any specific size. However, the area of the bottom surface is preferably 50 $cm^2$ to 2000 $cm^2$, more preferably 70 $cm^2$ to 1000 $cm^2$, even more preferably 90 $cm^2$ to 800 $cm^2$, and most preferably 110 $cm^2$ to 600 $cm^2$.

(2-2) Dispersion of Particulate Water-Absorbing Agent

In the measurement of the present invention, water absorbent property is evaluated after a particulate water-absorbing agent is dispersed on the bottom surface of the measurement device.

The dispersed particulate water-absorbing agent is immobilized, in whole or in part, so as not to move when the device is moved or when a liquid is introduced. A method of immobilizing the particulate water-absorbing agent is not limited to any specific method. However, as the method of immobilizing the particulate water-absorbing agent, a method of dispersing the particulate water-absorbing agent on an adhesive-coated sheet which has been adhered to the bottom surface of the device, a method of dispersing the particulate water-absorbing agent on a sheet coated in advance with an adhesive and then placing the sheet on the bottom surface of the device, or the like method can be employed. Examples of a method of preventing movement of the particulate water-absorbing agent without using any adhesive include a method of providing irregularities on the bottom surface of the device in such a degree that the horizontality of the bottom surface is not significantly impaired.

It is preferable that the particulate water-absorbing agent is dispersed as uniformly as possible. However, depending on the situation, it is possible to disperse a larger or smaller amount of particulate water-absorbing agent on a specific area. Further, in a case where the area of the bottom surface of the measurement device is large, it is possible to disperse a particulate water-absorbing agent on each of a plurality of sections into which the bottom surface is divided, in an amount weighed for each section, in order to further enhance uniformity.

The amount of the particulate water-absorbing agent dispersed with respect to the area of the bottom surface of the measurement container is preferably 50 g/m² to 1000 g/m², more preferably 80 g/m² to 800 g/m², and most preferably 100 g/m² to 600 g/m². If the amount of the particulate water-absorbing agent dispersed is smaller than the values in the above-described range, it may lead to an inaccurate evaluation. If the amount of the particulate water-absorbing agent dispersed is larger than the values in the above-described range, it may cause an excessively large thickness of a gel layer after swelling and lead to an inaccurate evaluation.

(2-3) Flat Plate and Pressure Condition

In a measurement method in accordance with the present invention, the dispersed particulate water-absorbing agent is caused to absorb an aqueous solution under pressure. Thus, a flat plate for applying pressure to a portion of the bottom surface (on which the particulate water-absorbing agent has been dispersed) of the measurement device is used.

The flat plate is equipped with an injection inlet for introducing an aqueous solution. The injection inlet is preferably shaped such that a cylindrical tube is placed in a center portion (center of gravity) of the flat plate. The height of the injection inlet is preferably a height that allows the injection inlet to have a capacity such that the injection inlet can retain an aqueous solution having been introduced into the tube until the aqueous solution is absorbed. The size of the injection inlet is preferably approximately 1% to 10% of the area of the flat plate.

The size of the flat plate is preferably a size such that the area of a portion to which pressure is applied by the flat plate is preferably 10% to 90% of the area of the bottom surface of the measurement container, more preferably 15% to 80% thereof, and most preferably 20% to 70% thereof.

It is preferable that a sheet is placed between the flat plate and the particulate water-absorbing agent, the sheet having voids of a size that allows an aqueous solution to pass therethrough but does not allow the particulate water-absorbing agent to pass therethrough. Placing the sheet makes it possible to prevent a swollen particulate water-absorbing agent from entering the injection inlet. A material of the sheet can be, for example, a metal gauze, nonwoven fabric, a gauze made of resin, and paper such as tissue paper.

A pressure condition (load) at the introduction of an aqueous solution, i.e. a pressure applied by the flat plate, is preferably 0.2 kPa to 10.0 kPa, more preferably 0.4 kPa to 8.0 kPa, even more preferably 0.6 kPa to 6.0 kPa, and most preferably 0.8 kPa to 5.0 kPa.

(2-4) Introduction of Liquid

In a measurement method in accordance with the present invention, an aqueous solution is introduced through the injection inlet with which the flat plate is equipped. The temperature of the aqueous solution is preferably 20° C. to 40° C. Further, the aqueous solution may be pure water, but has an electrical conductivity of preferably 2 mS/cm to 50 mS/cm, more preferably 5 mS/cm to 40 mS/cm, even more preferably 10 mS/cm to 30 mS/cm, and most preferably 13 mS/cm to 20 mS/cm.

A rate at which the aqueous solution is introduced is preferably 1 ml/sec to 50 ml/sec, more preferably 2 ml/sec to 40 ml/sec, more preferably 3 ml/sec to 30 ml/sec, particularly preferably 4 ml/sec to 20 ml/sec, and most preferably 5 ml/sec to 10 ml/sec.

It is preferable that the aqueous solution is introduced a plurality of times. Further, it is preferable that an equal amount of liquid is introduced each time. In a case where a liquid is introduced a plurality of times, the introduction is carried out at regular time intervals. The time interval at which the aqueous solution is introduced is preferably 1 minute to 180 minutes, more preferably 3 minutes to 120 minutes, and most preferably 5 minutes to 60 minutes.

The total amount of aqueous solution introduced is preferably 10 ml to 60 ml, more preferably 15 ml to 55 ml, and most preferably 20 ml to 50 ml, with respect to 1 g of the dispersed particulate water-absorbing agent.

(2-5) Measurement of Absorption Speed

In the present invention, the amount of time until the end of absorption of an aqueous solution introduced through the injection inlet by a particulate water-absorbing agent (absorption time) is measured. The amount of time until the end of absorption, which is the amount of time elapsed until the aqueous solution introduced through the injection inlet disappears from view, is measured as the amount of time (sec) elapsed from the introduction. It is preferable that the aqueous solution is colored (for example, colored blue) in order to allow easy observation of the aqueous solution.

(2-6) Measurement of Re-Wet

In the present invention, the re-wet of a liquid from the particulate water-absorbing agent having absorbed the liquid is measured in such a manner that, after the elapse of a predetermined period of time since the aqueous solution has been introduced, the flat plate is removed, the member capable of absorbing the aqueous solution is placed on the top of the particulate water-absorbing agent, pressure is applied for a predetermined period of time, and a mass of the aqueous solution absorbed by the component is measured.

The member capable of absorbing the aqueous solution can be, for example, cotton fabric, nonwoven fabric, foam such as sponge, and paper. Preferably, paper, more specifically, paper having stable quality, such as filter paper, is selected. Further, it is preferable that the re-wet is measured with use of sheets of paper the number or volume of which allows the re-wet to be measured adequately (i.e., sheets of paper the number or volume of which can prevent an absorption amount from being saturated).

The size (i.e., area) of the member capable of absorbing the aqueous solution is preferably 0.1 times to 3 times, more preferably 0.3 times to 2 times, and most preferably 0.5 to 1.5 times, with respect to the area of the flat plate for applying pressure.

The amount of time elapsed from the introduction of the aqueous solution to the start of application of pressure at the re-wet measurement is preferably 0.1 minutes to 60 minutes, more preferably 0.5 minutes to 30 minutes, and most preferably 1 minute to 15 minutes.

The length of time of application of pressure at the re-wet measurement is preferably 1 second to 60 seconds, more preferably 3 seconds to 50 seconds, and most preferably 5 seconds to 40 seconds.

The pressure applied at the re-wet measurement is preferably 1 kPa to 10 kPa, more preferably 2 kPa to 8 kPa, even more preferably 3 kPa to 7 kPa, and most preferably 4 kPa to 6 kPa. Further, the portion to which pressure is applied is preferably of a size half of the size of the member capable of absorbing the liquid to a size comparable to the size of the member capable of absorbing the liquid.

The re-wet is preferably 2.0 g or less, more preferably 1.7 g or less, even more preferably 1.5 g or less, and most preferably 1.3 g or less. In a case where a particulate water-absorbing agent having re-wet of greater than 2.0 g is used as an absorbent body in a sanitary material such as a diaper, the re-wet of a body fluid such as urine in the absorbent body increases. This may cause skin irritation, rash, and urine leakage.

[3] Method of Producing Particulate Water-Absorbing Agent

The following description will discuss steps (3-1) to (3-9) for producing a particulate water-absorbing agent in accordance with an embodiment of the present invention.

(3-1) Step of Preparing Aqueous Monomer Solution

This step is a step of preparing an aqueous solution containing a monomer (e.g., an acrylic acid (salt)) as a main component (this solution is hereinafter referred to as an "aqueous monomer solution"). It is also possible to use a monomer slurry liquid to the extent that a water-absorbing resin to be produced will not have degraded water absorption performance. For convenience of description, however, this section describes an aqueous monomer solution.

The term "main component" means that the acrylic acid (salt) is used (contained) in an amount of ordinarily 50 mol % or more, preferably 70 mol % or more, more preferably 90 mol % or more (with an upper limit of 100 mol %), per a total amount of monomers used for a polymerization reaction of a water-absorbing resin (excluding an internal crosslinking agent).

(Acrylic Acid)

For the present invention, it is preferable that an acrylic acid and/or an acrylic acid salt (hereinafter referred to as "acrylic acid (salt)") is used as a monomer from the viewpoint of physical properties of a particulate water-absorbing agent to be produced and productivity. The "acrylic acid" may be a publicly-known acrylic acid, and contains, as a polymerization inhibitor, preferably a methoxyphenol, and more preferably p-methoxyphenol. The acrylic acid (salt) only needs to contain such a polymerization inhibitor in an amount of preferably 200 ppm or less, more preferably 10 ppm to 160 ppm, even more preferably 20 ppm to 100 ppm, from the viewpoint of polymerizability of the acrylic acid and the color of a particulate water-absorbing agent to be produced. An impurity in the acrylic acid for the present invention may be a compound disclosed in U.S. Patent Application Publication No. 2008/0161512.

The "acrylic acid salt" is a compound produced by neutralizing the above acrylic acid with a basic composition below. The acrylic acid salt may be a commercially available acrylic acid salt (for example, sodium acrylate) or may be an acrylic acid salt produced by neutralizing an acrylic acid in a plant for producing a particulate water-absorbing agent.

(Basic Composition)

In the present invention, the term "basic composition" refers to a composition containing a basic compound, such as a commercially available aqueous sodium hydroxide solution.

Specific examples of the basic compound encompass a carbonate or bicarbonate of an alkali metal, a hydroxide of an alkali metal, ammonia, and organic amine. Among these, the basic compound preferably has strong basicity from the viewpoint of physical properties of a particulate water-absorbing agent to be obtained. That is, the basic compound is preferably a hydroxide of alkali metal, such as sodium hydroxide, potassium hydroxide, or lithium hydroxide, and is more preferably sodium hydroxide.

(Neutralization)

In the present invention, neutralization can be neutralization of an acrylic acid (before polymerization), neutralization of a crosslinked hydrogel polymer obtained by crosslinking and polymerizing an acrylic acid (after polymerization) (hereinafter referred to as "later neutralization"), or a combination of the neutralization of an acrylic acid and the neutralization of a crosslinked hydrogel polymer obtained by crosslinking and polymerizing an acrylic acid. These neutralizations are not limited to any particular type, and can be of a continuous type or a batch type. Among these, a continuous type is preferable from the viewpoint of production efficiency and the like.

Note that with regard to conditions such as a neutralization apparatus, a neutralization temperature, and a retention time, the conditions disclosed in International Publication No. WO 2009/123197 and U.S. Patent Application Publication No. 2008/0194863 can be applied to the present invention.

A neutralization rate in the present invention is preferably 10 mol % to 90 mol %, more preferably 40 mol % to 85 mol %, even more preferably 50 mol % to 80 mol %, and particularly preferably 60 mol % to 75 mol % per an acid group of a monomer. At a neutralization rate of less than 10 mol %, a fluid retention capacity may be lowered significantly. Meanwhile, in a case where the neutralization rate is higher than 90 mol %, a high-performance water-absorbing resin may not be obtained.

The neutralization rate also applies to the later neutralization. The neutralization rate can also apply to a neutralization rate for a particulate water-absorbing agent which is an end product. Note that a neutralization rate of 75 mol % means a mixture of 25 mol % of an acrylic acid and 75 mol % of an acrylic acid salt. The mixture is referred to also as a partially neutralized acrylic acid.

(Other Monomer(s))

In the present invention, "other monomer(s)" refers to a monomer(s) other than the acrylic acid (salt), and refers to a monomer(s) which can be used in combination with the acrylic acid (salt) to produce a particulate water-absorbing agent. Examples of the other monomer(s) encompass an unsaturated monomer which is water-soluble or hydrophobic. Specifically, the compound disclosed in U.S. Patent Application Publication No. 2005/0215734 (except an acrylic acid) can be applied to the present invention.

(Internal Crosslinking Agent)

The compounds disclosed in U.S. Pat. No. 6,241,928 can be used as an internal crosslinking agent usable in the present invention. One of the compounds or two or more of the compounds is/are to be selected in view of reactivity.

From the viewpoint of, for example, the water absorption performance of a water-absorbing resin to be produced, the internal crosslinking agent is preferably a compound having two or more polymerizable unsaturated groups, more preferably a compound that is pyrolytic at a drying temperature (described later), even more preferably a compound having a (poly)alkylene glycol structural unit and two or more polymerizable unsaturated groups.

The polymerizable unsaturated groups are preferably an allyl group or a (meth)acrylate group, more preferably a (meth)acrylate group. The (poly)alkylene glycol structural unit is preferably polyethylene glycol. The n number of the (poly)alkylene glycol is preferably 1 to 100, more preferably 6 to 50.

Therefore, in an embodiment of the present invention, the internal crosslinking agent to be used is preferably (poly)alkylene glycol di(meth)acrylate or (poly)alkylene glycol tri(meth)acrylate, and more preferably (poly)ethylene glycol di(meth)acrylate.

The internal crosslinking agent is to be used in an amount of preferably 0.0001 mol % to 10 mol %, more preferably 0.001 mol % to 1 mol % relative to a total amount of monomers. In a case where the amount used falls within the above ranges, a desired water-absorbing resin can be obtained. Note that in a case where the amount used is excessively small, gel strength tends to be lowered and consequently there tends to be an increase in water-soluble content. In a case where the used amount is excessively large, fluid retention capacity tends to be lowered. Therefore, the amount used that is excessively large or excessively small is not preferable.

For the present invention, the following method is preferably used: An aqueous monomer solution to which a certain amount of internal crosslinking agent has been added in advance is prepared. Then, the aqueous monomer solution is simultaneously subjected to polymerization and to a crosslinking reaction. Alternatively, other than the above method, examples of a possible method encompass a method in which an internal crosslinking agent is added during or after the polymerization so that postcrosslinking is carried out, a method in which radical crosslinking is carried out with use of a radical polymerization initiator, and a method in which radiation crosslinking is carried out with use of active energy rays such as an electron ray and an ultraviolet ray. Alternatively, these methods may be used in combination. Alternatively, these methods can be used in combination.

(Other Substances Added to Aqueous Monomer Solution)

In an embodiment of the present invention, from the viewpoint of improving physical properties of a water-absorbing resin to be produced, any of the below substances can be added to the aqueous monomer solution during the preparation thereof.

Specifically, a hydrophilic polymer such as starch, a starch derivative, cellulose, a cellulose derivative, polyvinyl alcohol, polyacrylic acid (salt), and crosslinked polyacrylic acid (salt) can be added in an amount of preferably 50 mass % or less, more preferably 20 mass % or less, even more preferably 10 mass % or less, and particularly preferably 5 mass % or less (with the lower limit of 0 mass %). A carbonate, an azo compound, a foaming agent such as a gas bubble, a surfactant, a chelating agent, a chain transfer agent, and the like can be added in an amount of preferably 5 mass % or less, more preferably 1 mass % or less, and even more preferably 0.5 mass % or less (with the lower limit of 0 mass %).

In an embodiment of the present invention, from the viewpoint of improving physical properties of a water-absorbing resin to be produced, $\alpha$-hydroxycarboxylic acid (salt) can be added to the aqueous monomer solution during the preparation thereof.

($\alpha$-Hydroxycarboxylic Acid (Salt))

Ordinarily, from the viewpoint of the water absorbent property, color (coloring prevention), and the like in the water-absorbing agent to be produced, it is preferable to add $\alpha$-hydroxycarboxylic acid (salt). Addition of $\alpha$-hydroxycarboxylic acid (salt) reduces the molecular weight of a water-soluble content in a water-absorbing agent to be produced, and accordingly reduces stickiness and discomfort during use of the water-absorbing agent as a hygienic material. Thus, from these further viewpoints, it is preferable to add $\alpha$-hydroxycarboxylic acid (salt). Note that "$\alpha$-hydroxycarboxylic acid (salt)" is a carboxylic acid having a hydroxyl group in a molecule or is a salt thereof, and is a hydroxycarboxylic acid having a hydroxyl group at an alpha position or is a salt thereof.

Specifically, as the $\alpha$-hydroxycarboxylic acid (salt), a compound and an amount used thereof disclosed in "[6] $\alpha$-hydroxycarboxylic acid compound" of International Publication No. WO 2011/040530 can be applied to the present invention.

In a case where a water-soluble resin or a water-absorbing resin is used as the hydrophilic polymer, a graft polymer or a water-absorbing resin composition (for example, a polymer produced from starch and an acrylic acid, a polymer produced from PVA and an acrylic acid, and the like) can be obtained. These polymers and water-absorbing resin compositions are also encompassed in the scope of the present invention.

(Monomer Component Concentration)

The above various substances are added during the step of preparing an aqueous monomer solution. The aqueous monomer solution may contain a monomer component at any concentration. The concentration is, however, within a range of preferably 10 mass % to 80 mass %, more preferably 20 mass % to 75 mass %, even more preferably 30 mass % to 70 mass %, from the viewpoint of physical properties of a water-absorbing resin to be produced.

In a case where aqueous solution polymerization or reversed phase suspension polymerization is employed, a solvent other than water can be used in combination as necessary. In such a case, the type of the solvent used is not limited to any particular one.

The "monomer component concentration" is a value determined by Formula 6 below. The mass of the aqueous monomer solution does not include the mass of a graft component, water-absorbing resin, or a hydrophobic solvent used in reversed phase suspension polymerization.

Monomer component concentration (mass %)=(mass of monomer component)/(mass of aqueous monomer solution)×100     Formula 6.

(3-2) Polymerization Step

This step is a step of polymerizing an acrylic acid (salt)-based aqueous monomer solution obtained in the step of preparing the aqueous monomer solution, so that a crosslinked hydrogel polymer (hereinafter referred to as "hydrogel") is obtained.

(Polymerization Initiator)

The polymerization initiator usable in the present invention is selected as appropriate in accordance with a form of polymerization or the like and is not limited to any particular one. Examples of the polymerization initiator encompass a pyrolytic polymerization initiator, a photolytic polymerization initiator, and a redox-type polymerization initiator that contains a reducing agent for facilitating decomposition of any of those polymerization initiators. Specifically, used as the polymerization initiator is one of the polymerization initiators disclosed in U.S. Pat. No. 7,265,190, or a compound of two or more of the polymerization initiators disclosed in U.S. Pat. No. 7,265,190. Further, the polymerization initiator is preferably a peroxide or an azo compound, more preferably a peroxide, and even more preferably a persulfate, from the viewpoint of the handleability of the polymerization initiator and the physical properties of the particulate water-absorbing agent or the water-absorbing resin.

The amount of the polymerization initiator to be used ranges from preferably 0.001 mol % to 1 mol %, and more preferably 0.001 mol % to 0.5 mol %, relative to the amount of monomers. The amount of the reducing agent to be used ranges from preferably 0.0001 mol % to 0.02 mol %, relative to the amount of monomers.

A polymerization reaction can be carried out by, instead of using the polymerization initiator, irradiating a monomer with an active energy ray such as a radial ray, an electron ray, or an ultraviolet ray. Alternatively, any of these active energy rays can be used in combination with a polymerization initiator.

(Form of Polymerization)

Polymerization to be applied to the present invention is not limited to any particular form. From the viewpoint of a water absorbent property, ease of control of polymerization, and the like, preferable examples of the polymerization encompass spray droplet polymerization, aqueous solution polymerization, and reversed phase suspension polymerization, more preferable examples of the polymerization encompass aqueous solution polymerization and reverse phase suspension polymerization, and even more preferable examples of the polymerization encompass aqueous solution polymerization. Among these, continuous aqueous solution polymerization is particularly preferable. The continuous aqueous solution polymerization can be any one of continuous belt polymerization and continuous kneader polymerization.

Specific examples of the form of continuous belt polymerization encompass those disclosed in U.S. Pat. Nos. 4,893,999, 6,241,928, and U.S. Patent Application Publication No. 2005/0215734. Specific examples of the form of continuous kneader polymerization encompass those disclosed in U.S. Pat. Nos. 6,987,151 and 6,710,141. In a case where these forms of continuous aqueous solution polymerization are employed, it is possible to improve efficiency with which a water-absorbing resin is produced.

Preferable examples of the form of the continuous aqueous solution polymerization encompass "high-temperature-initiating polymerization" and "high-concentration polymerization". The "high-temperature-initiating polymerization" is a form of polymerization in which polymerization is started while a temperature of an aqueous monomer solution is preferably 30° C. or higher, more preferably 35° C. or higher, even more preferably 40° C. or higher, and especially even more preferably 50° C. or higher (upper limit: boiling point). The "high-concentration polymerization" is a form of polymerization in which polymerization is carried out while a monomer concentration is preferably 30 mass % or more, more preferably 35 mass % or more, even more preferably 40 mass % or more, and especially even more preferably 45 mass % or more (upper limit: saturating concentration). Alternatively, it is possible to use these forms of polymerization in combination.

In an embodiment of the present invention, polymerization can be carried out in an air atmosphere. From the viewpoint of color of a water-absorbing resin to be produced, polymerization is to be carried out preferably in an atmosphere of inert gas such as nitrogen or argon. In such a case, an oxygen concentration is preferably controlled to be, for example, 1 volume % or less. Note that dissolved oxygen in an aqueous monomer solution is also preferably substituted with inert gas (e.g., dissolved oxygen: less than 1 mg/l).

In an embodiment of the present invention, alternatively, it is possible to carry out foaming polymerization in which polymerization is carried out while gas bubbles (particularly the inert gas or the like) are dispersed into an aqueous monomer solution.

In an embodiment of the present invention, alternatively, it is possible to increase a solid content concentration during polymerization. A degree of increase in solid content as an index of an increase in such a solid content concentration can be defined by the following Formula 7. Note that the degree of increase in solid content is preferably 1 mass % or more, and more preferably 2 mass % or more.

Degree (mass %) of increase in solid content=(solid content concentration in hydrogel after polymerization)−(solid content concentration in aqueous monomer solution)   Formula 7

The solid content concentration in an aqueous monomer solution is a value that can be obtained by the following Formula 8. Components in a polymerization system are an aqueous monomer solution, a graft component, a water-absorbing resin, and other solid matters (e.g., water-insoluble fine particles and the like). The components in the polymerization system exclude a hydrophobic solvent in reverse phase suspension polymerization.

Solid content concentration (mass %) in aqueous monomer solution={(mass of monomer component+graft component+water-absorbing resin+other solid matters)/(mass of components in polymerization system)}×100   Formula 8

(3-3) Gel-Crushing Step

This step is a step of gel-crushing a hydrogel, which has been obtained by the polymerization step, with use of, for example, a kneader, a screw extruder such as a meat chopper, or a gel-crusher such as a cutter mill in order to obtain a hydrogel in the form of particles (hereinafter referred to as "particulate hydrogel"). In a case where the polymerization step is carried out through kneader polymerization, such a step is equivalent to a combination of the polymerization step and the gel-crushing step which are carried out simultaneously. In a case where a particulate hydrogel is directly obtained through a polymerization process such as vapor phase polymerization or reverse phase suspension polymerization, the gel-crushing step may not be carried out.

With regard to gel-crushing conditions and forms other than above described, reference can be made to the disclosure of International Publication No. WO 2011/126079.

(3-4) Drying Step

This step is a step of drying the particulate hydrogel, which has been obtained by the polymerization step and/or the gel-crushing step, until a desired resin solid content is attained, so as to obtain a dried polymer. The resin solid content is calculated from drying loss (a change in mass after heating 1 g of the water-absorbing resin at 180° C. for three hours). The resin solid content is preferably 80 mass % or more, more preferably in a range of 85 mass % to 99 mass %, even more preferably in a range of 90 mass % to 98 mass %, and especially even more preferably in a range of 92 mass % to 97 mass %.

A drying method of drying the particulate hydrogel is not particularly limited. Examples of the drying method encompass thermal drying, hot air drying, drying under reduced pressure, fluidized bed drying, infrared drying, microwave drying, drum dryer drying, drying by azeotropic dehydration with a hydrophobic organic solvent, and high humidity drying by use of high temperature water vapor. The drying method is, among others, preferably hot air drying, more preferably band drying, in which hot air drying is performed on a through-flow belt, from the viewpoint of drying efficiency.

From the viewpoint of the color of a water-absorbing resin to be produced and drying efficiency, hot air drying is performed at a drying temperature (temperature of hot air) of preferably 120° C. to 250° C., more preferably 150° C. to 200° C. Drying conditions other than the drying temperature (e.g., the air velocity of hot air and the drying time) can be set as appropriate in accordance with moisture content of the particulate hydrogel to be dried, total mass of the particulate hydrogel to be dried, and a desired resin solid content. In the case of band drying, the various conditions disclosed in, for example, International Publication No. WO 2006/100300, International Publication No. WO 2011/025012, International Publication No. WO 2011/025013, and International Publication No. WO 2011/111657 can be applied as necessary.

Setting the drying temperature and the drying time to be within these ranges makes it possible to obtain a water-absorbing resin whose CRC (centrifuge retention capacity), water-soluble content (Ext), and color are within a desired range (see [5] below).

(3-5) Pulverization Step and Classification Step

This step is a step of pulverizing (pulverization step) the dried polymer obtained in the drying step and adjusting (classification step) the particle size of a resulting pulverized polymer to be a particle size within a certain range so that a water-absorbing resin powder is obtained (for convenience, water-absorbing resin in a powder form before being subjected to surface crosslinking is referred to as "water-absorbing resin powder").

An apparatus used in the pulverization step of the present invention can be, for example, a high-speed crusher such as a roll mill, a hammer mill, a screw mill, and a pin mill; a vibrating mill; a knuckle-type crusher; a cylindrical mixer; and the like. These apparatuses can be used in combination according to need.

A particle size adjusting method in the classification step of the present invention is not limited to a particular one and can be, for example, sieve classification with use of a JIS standard sieve (JIS Z8801-1 (2000)), airflow classification, or the like. Note that the particle size of water-absorbing resin is not limited to being adjusted during the pulverization step and classification step, but may alternatively be adjusted as appropriate during the polymerization step (in particular, in reversed phase suspension polymerization or spray droplet polymerization) or other steps (for example, a granulation step or a fine powder recycling step).

The water-absorbing resin powder obtained in the present invention has a mass average particle diameter (D50) which ranges preferably from 200 µm to 600 µm, more preferably 200 µm to 550 µm, even preferably 250 µm to 500 µm, and particularly preferably 350 µm to 450 µm. The water-absorbing resin powder contains particles with a particle diameter of less than 150 µm at a proportion of preferably 10 mass % or less, more preferably 5 mass % or less, and even more preferably 1 mass % or less. The water-absorbing resin powder contains particles with a particle diameter of 850 µm or more at a proportion of preferably 5 mass % or less, more preferably 3 mass % or less, and even more preferably 1 mass % or less. A lower limit value of each of the proportions of such particles is preferably as low as possible and is desirably 0 mass %. Note, however, that a lower limit of each of the proportions of such particles can be approximately 0.1 mass %. The water-absorbing resin powder has a logarithmic standard deviation (σξ) of a particle size distribution which falls in a range of preferably 0.20 to 0.50, more preferably 0.25 to 0.40, and still more preferably 0.27 to 0.35. Note that these particle sizes are measured with use of a standard sieve in conformity with a measuring method disclosed in U.S. Pat. No. 7,638,570 or EDANA ERT 420.2-02.

The above particle sizes apply not only to water-absorbing resin subsequent to surface crosslinking (for convenience, hereinafter referred to also as "water-absorbing resin particle(s)"), but also to a particulate water-absorbing agent as a final product. Therefore, it is preferable to subject the water-absorbing resin particles to surface crosslinking (surface-crosslinking step) so that the particle size falling within the above described range is maintained, and it is more preferable to carry out particle size adjustment by carrying out a sizing step subsequent to the surface-crosslinking step.

(3-6) Surface-Crosslinking Step

This step is a step of forming a portion with a higher crosslinking density in a surface layer (that is, a portion of the water-absorbing resin powder which portion is up to several tens of micrometers deep from the surface) of the water-absorbing resin powder produced through the above steps. This step includes a mixing step, a heat treatment step, and optionally a cooling step.

In the surface-crosslinking step, a water-absorbing resin (water-absorbing resin particles) can be obtained which has been surface-crosslinked by radical crosslinking on the surface of the water-absorbing resin powder, surface polymerization on the surface of the water-absorbing resin powder, crosslinking reaction with a surface-crosslinking agent, or the like.

(Surface-Crosslinking Agent)

A surface-crosslinking agent used in the present invention is not limited to any particular one. Examples of the surface-crosslinking agent encompass an organic surface-crosslinking agent and an inorganic surface-crosslinking agent. Among others, an organic surface-crosslinking agent that is reactive with a carboxyl group is preferable, from the viewpoint of the physical properties of a water-absorbing resin and the handleability of the surface-crosslinking agent. For example, one of the surface-crosslinking agents disclosed in U.S. Pat. No. 7,183,456 can be used, or two or more of the surface-crosslinking agents disclosed in U.S. Pat. No. 7,183,456 can be used. Specifically, examples of the surface-crosslinking agent encompass a polyhydric alcohol compound, an epoxy compound, a haloepoxy compound, a polyamine compound, a condensed product with a haloepoxy compound of the polyamine compound, an oxazoline compound, an oxazolidinone compound, a polyvalent metal salt, an alkylene carbonate compound, a cyclic urea compound, and the like.

An amount of the surface-crosslinking agent used (or a total amount used in a case where a plurality of surface-crosslinking agents are used) is preferably 0.01 parts by mass to 10 parts by mass, more preferably 0.01 parts by mass to 5 parts by mass, relative to 100 parts by mass of the water-absorbing resin powder. The surface-crosslinking agent is preferably added as an aqueous solution. In such a case, an amount of water used is preferably 0.1 parts by mass to 20 parts by mass, and more preferably 0.5 parts by mass to 10 parts by mass, relative to 100 parts by mass of the water-absorbing resin powder. In a case where a hydrophilic organic solvent is used according to need, an amount of the hydrophilic organic solvent used is preferably 10 parts by mass or less, and more preferably 5 parts by mass or less, relative to 100 parts by mass of the water-absorbing resin powder.

It is possible to mix additives, which are added in a "remoistening step" described below, with the surface-crosslinking agent (aqueous solution) by adding each of the additives in a range of equal to or less than 5 parts by mass. Alternatively, it is possible to add the additives to the water-absorbing resin powder and the surface-crosslinking agent in a different mixing step described below.

(Mixing Step)

This step is a step of mixing the water-absorbing resin powder and the surface-crosslinking agent. A method of mixing the surface-crosslinking agent is not limited to a particular one and can be a method in which a surface-crosslinking agent solution is prepared in advance, and the surface-crosslinking agent solution is mixed with the water-absorbing resin powder preferably by spraying or dropping the surface-crosslinking agent solution onto the water-absorbing resin powder, more preferably by spraying the surface-crosslinking agent solution onto the water-absorbing resin powder.

The above mixing may be performed with use of any device. The device is preferably a high-speed stirring mixer, more preferably a high-speed stirring continuous mixer.

(Heat Treatment Step)

This step is a step of heating a mixture, which has been obtained in the mixing step, so as to cause crosslinking reaction on a surface of the water-absorbing resin powder.

An apparatus for performing the crosslinking reaction is not limited to any particular one, and can be preferably a paddle dryer. A reaction temperature in the crosslinking reaction is set as appropriate according to a type of a used surface-crosslinking agent, and is preferably 50° C. to 300° C., and more preferably 100° C. to 200° C.

(Cooling Step)

This step is an optional step which is provided after the heat treatment step if needed.

An apparatus for carrying out the cooling is not limited to a particular one and is preferably an apparatus whose specification is identical with that of an apparatus used in the heat treatment step, and more preferably a paddle dryer. This is because such an apparatus can be used as a cooling apparatus by replacing a heating medium with a refrigerant. Note that, according to need, the water-absorbing resin particles obtained in the heat treatment step are force-cooled in the cooling step to a temperature preferably of 40° C. to 80° C., and more preferably of 50° C. to 70° C.

(3-7) Remoistening Step

This step is a step of adding, to the water-absorbing resin particles obtained in the surface-crosslinking step, at least one additive selected from the group consisting of water-insoluble inorganic fine particles described below, a polyvalent metal salt, a cationic polymer, a chelating agent, an inorganic reducing agent, the above described hydroxycarboxylic acid compound, and the above described moisture absorption fluidity improving agent.

Note that in a case where the additive is added in the form of aqueous solution or slurry liquid, the water-absorbing resin particles are swollen by water again. Therefore, this step is also referred to as "remoistening step". Further, as described above, the additive can be mixed with the water-absorbing resin powder simultaneously with the surface-crosslinking agent (aqueous solution).

(Water-Insoluble Inorganic Fine Particles, Polyvalent Metal Salt, and Cationic Polymer)

In an embodiment of the present invention, it is preferable to add one or more additives selected from water-insoluble inorganic fine particles, a polyvalent metal salt, and a cationic polymer, from the viewpoint of improvement in, for example, absorption speed, liquid permeability, and moisture absorption fluidity of a water-absorbing resin to be produced.

As the polyvalent metal salt and the cationic polymer, a compound and an amount used thereof disclosed in "[7] Polyvalent metal salt and/or cationic polymer" of International Publication No. WO 2011/040530 can be applied to the present invention. As the water-insoluble inorganic fine particles, a compound disclosed in "[5] Water-insoluble inorganic fine particles" of International Publication No. WO 2011/040530 can be applied to the present invention.

(Chelating Agent)

In an embodiment of the present invention, it is preferable to add a chelating agent from the viewpoint of, for example, color (coloring prevention) and deterioration prevention in a water-absorbing resin to be produced.

Specifically, as the chelating agent, a compound and an amount used thereof disclosed in "[2] Chelating agent" of International Publication No. WO 2011/040530 can be applied to the present invention.

(Inorganic Reducing Agent)

In an embodiment of the present invention, it is preferable to add an inorganic reducing agent from the viewpoint of, for example, color (coloration prevention), deterioration prevention, and reduction in residual monomers in a water-absorbing resin to be produced.

Specifically, as the inorganic reducing agent, a compound and an amount used thereof disclosed in "[3] Inorganic reducing agent" of International Publication No. WO 2011/040530 can be applied to the present invention.

(3-8) Step of Adding Another Additive

In the present invention, an additive other than the above described additives can be added in order to give various functions to the water-absorbing resin to be obtained. Specifically, examples of such an additive encompass a surfactant, a compound having a phosphorus atom, an oxidizer, an organic reducing agent, organic powder such as metallic soap, a deodorant agent, an antibacterial agent, pulp, thermoplastic fibers, and the like. Note that, as the surfactant, a compound disclosed in International Publication No. WO 2005/075070 can be applied to the present invention.

An amount of the additive used (added) is determined as appropriate according to a purpose of the additive, and is therefore not limited to a particular one. The amount used (added) of the additive is preferably 3 parts by mass or less, and more preferably 1 part by mass or less, relative to 100 parts by mass of the water-absorbing resin powder. It is also possible to add the additive during a step other than the above step.

(3-9) Other Steps

In the present invention, in addition to the above described steps, it is possible to carry out a granulation step, a sizing step, a fine powder removal step, a fine powder recycling step, and the like according to need. Moreover, it is possible to further carry out one or more of a transportation step, a storing step, a packing step, a reserving step, and the like. Note that the "sizing step" encompasses a fine powder removal step subsequent to the surface-crosslinking step and a step of carrying out classification and pulverization in a case where a water-absorbing resin is aggregated to have a size larger than an intended size. The "fine powder recycling step" encompasses an aspect in which fine powder itself is added as in the present invention, and also a step of adding the fine powder, in the form of a large hydrogel, during any of the steps for producing the water-absorbing resin.

[4] Application of Particulate Water-Absorbing Agent

An application of a particulate water-absorbing agent of the present invention is not limited to any particular one. However, the particulate water-absorbing agent is preferably used as an absorbent body in sanitary materials such as disposable diapers, sanitary napkins, and incontinence pads. In particular, the particulate water-absorbing agent can be used as an absorbent body in high-concentration disposable diapers (i.e., disposable diapers each of which contains a large amount of the particulate water-absorbing agent) having problems such as odor derived from a raw material and coloring. Further, in a case where the particulate water-absorbing agent is used as an upper layer part of the absorbent body, a significant effect can be expected.

Alternatively, as the absorbent body, it is possible to use an absorbent material such as a pulp fiber, in addition to the particulate water-absorbing agent. In such a case, an amount (core concentration) of the particulate water-absorbing agent contained in the absorbent body is preferably 30 mass % to 100 mass %, more preferably 40 mass % to 100 mass %, still more preferably 50 mass % to 100 mass %, further still more preferably 60 mass % to 100 mass %, particularly preferably 70 mass % to 100 mass %, and most preferably 75 mass % to 95 mass %.

In a case where the core concentration falls within the above range and the absorbent body is used as an upper layer part of an absorbent article, the absorbent article can maintain cleanness, i.e., a state of being white. Further, in such a case, the absorbent article is excellent in diffusion property with respect to a body fluid or the like such as urine or blood, and therefore improvement in absorption amount can be expected based on efficient liquid distribution.

[5] Properties of Preferable Particulate Water-Absorbing Agent

The following description will discuss properties (physical properties) of a preferable particulate water-absorbing agent of the present invention. The physical properties below are measured in accordance with EDANA method unless otherwise specified.

(5-1) Index of DRC

Index of DRC is defined by the following Formula 1.

Index of DRC=(49−DRC5 min)/(D50/1000)　　　Formula 1

The index of DRC is 43 or less, 42 or less, 41 or less, 40 or less, 39 or less, 38 or less, 37 or less, 36 or less, 35 or less, 34 or less, 33 or less, 32 or less, 31 or less, 30 or less, 29 or less, 28 or less, 27 or less, 26 or less, 25 or less, 24 or less, 23 or less, 22 or less, 21 or less, 20 or less, 19 or less, 18 or less, 17 or less, 16 or less, 15 or less, 14 or less, 13 or less, 12 or less, 11 or less, 10 or less, 9 or less, 8 or less, 7 or less, 6 or less, 5 or less, 4 or less, 3 or less, 2 or less, or 1 or less. The index of DRC is preferably −5 or more or 0 or more.

(5-2) DRC5 Min (Dunk Retention Capacity 5 Minutes)

The DRC5 min of the particulate water-absorbing agent of the present invention is not particularly limited, provided that the above described index of DRC is satisfied. It is preferable, however, that the DRC5 min is 35 g/g or more, 38 g/g or more, or 40 g/g or more. An upper limit of the DRC5 min is not particularly limited but is ordinarily 60 g/g or less, or 55 g/g or less.

(5-3) Centrifuge Retention Capacity (CRC)

A centrifuge retention capacity (CRC) of the particulate water-absorbing agent of the present invention is 30 g/g to 50 g/g, and is preferably 31 g/g to 50 g/g, 32 g/g to 50 g/g, 33 g/g to 50 g/g, 34 g/g to 50 g/g, 35 g/g to 50 g/g, 36 g/g to 50 g/g, 30 g/g to 49 g/g, 30 g/g to 48 g/g, 30 g/g to 47 g/g, 30 g/g to 46 g/g, 30 g/g to 45 g/g, 30 g/g to 44 g/g, 30 g/g to 43 g/g, 30 g/g to 42 g/g, 30 g/g to 41 g/g, 30 g/g to 40 g/g, 30 g/g to 39 g/g, and 30 g/g to 38 g/g.

If the CRC is less than 5 g/g, then an absorption amount is small. This renders a particulate water-absorbing agent unsuitable as an absorbent body of a sanitary material such as a disposable diaper. If the CRC is more than 70 g/g, then a rate at which, for example, a body fluid such as urine or blood is absorbed decreases. This renders a particulate water-absorbing agent unsuitable for use in, for example, a disposable diaper having a high absorption speed. Note that the CRC can be controlled with use of, for example, an internal crosslinking agent and a surface-crosslinking agent.

(5-4) Particle Size (Particle Size Distribution, Mass Average Particle Diameter (D50), and Logarithmic Standard Deviation (σξ) of Particle Size Distribution)

The particulate water-absorbing agent of the present invention has a particle size (a particle size distribution, a mass average particle diameter (D50), and a logarithmic standard deviation (σξ) of the particle size distribution) which is controlled so as to be the same as the particle size of the water-absorbing resin powder before being subjected to surface crosslinking. A preferable particle size is as described in "(3-5) Pulverization step and classification step" above.

(5-5) Surface Tension

The particulate water-absorbing agent of the present invention has a surface tension (defined by a measuring method described in the Examples) of 65 mN/m or more, preferably 66 mN/m or more, more preferably 67 mN/m or more, even more preferably 68 mN/m or more, still even more preferably 69 mN/m or more, yet even more preferably 70 mN/m or more, particularly preferably 71 mN/m or more, and most preferably 72 mN/m or more. Ordinarily, 75 mN/m is sufficient as an upper limit of the surface tension. Satisfying the above conditions of surface tension allows for a reduction in re-wet of a disposable diaper.

(5-6) Particle Shape

According to a preferred embodiment, the particle shape of the particulate water-absorbing agent of the present invention is a non-uniformly pulverized shape. This is because: a particulate water-absorbing agent having a non-uniformly pulverized shape has a specific surface area larger than that of spherical particles obtained by a reversed phase suspension polymerization or a vapor phase polymerization so that the particulate water-absorbing agent has higher absorption speed; and a particulate water-absorbing agent having a non-uniformly pulverized shape can be more easily fixed to a pulp than in the case of spherical particles.

(5-7) Moisture Absorption Fluidity (Moisture Adsorption Blocking Ratio) (B.R.)

A specific method of measuring (evaluating) moisture adsorption fluidity (B.R.) will be described in Examples. The particulate water-absorbing agent of the present invention has moisture adsorption fluidity (B.R.) of ordinarily 50 mass % or less, preferably 40 mass % or less, more preferably 30 mass % or less, even more preferably 20 mass % or less, still even more preferably 10 mass % or less, and most preferably 0 mass %. The moisture absorption fluidity (B.R.) of the particulate water-absorbing agent of the present invention can be 0 mass % to 50 mass %, 0 mass % to 40 mass %, 0 mass % to 30 mass %, 0 mass % to 20 mass %, or 0 mass % to 10 mass %. If the moisture absorption fluidity (B.R.) is more than 50 mass %, then the particulate water-absorbing agent is difficult to handle in humid conditions. This may pose a problem that, during production of a thin absorbent body for hygienic material, for example, the particulate water-absorbing agent aggregates in a transport pipe in a production plant and therefore the transport pipe clogs and/or the particulate water-absorbing agent cannot be uniformly mixed with hydrophilic fibers. In a case where the condition above is satisfied, it becomes possible to decrease the adherence of the particulate water-absorbing agent to equipment when an absorbent body is produced with use of the particulate water-absorbing agent and hydrophilic fibers (fiber material).

(5-8) Water-Soluble Content (Ext)

According to a preferred embodiment, the particulate water-absorbing agent of the present invention has a water-soluble content (Ext) of 25 mass % or less, preferably 24 mass % or less, more preferably 22 mass % or less, and even more preferably 20% mass % or less. In a case where the particulate water-absorbing agent satisfies the above condition, an absorbing ability (e.g., fluid retention capacity under pressure) of the particulate water-absorbing agent improves. Therefore, in a case where the particulate water-absorbing agent is used in a disposable diaper, performance can be improved (such as a reduction in re-wet).

(5-9) Degradable Soluble Content

According to a preferred embodiment, the particulate water-absorbing agent of the present invention has a degradable soluble content of 30 mass % or less, preferably 27 mass % or less, more preferably 24 mass % or less, and even more preferably 20% mass % or less. In a case where the particulate water-absorbing agent satisfies the above condition, urine resistance improves. Therefore, in a case where the particulate water-absorbing agent is used in a disposable diaper, problems caused by a body fluid such as urine can be prevented, examples of which encompass gel deterioration, skin irritation, rash, and a decrease in odor-removing ability.

(5-10) Fluid Retention Capacity Under Pressure (AAP)

The particulate water-absorbing agent of the present invention has a fluid retention capacity under pressure (AAP) of preferably 18 g/g or more, more preferably 22 g/g or more, even more preferably 24 g/g or more, particularly preferably 26 g/g or more, more particularly preferably 28 g/g or more, and most preferably 30 g/g or more. The upper limit value of the fluid retention capacity under pressure (AAP) is not limited to any particular value, but is preferably 40 g/g or less.

If the AAP is less than 18 g/g, then the re-wet of a liquid when a pressure is applied to an absorbent body becomes large. This means that such a particulate water-absorbing agent is unsuitable as an absorbent body of a sanitary material such as a disposable diaper. Note that AAP can be controlled with use of particle size, surface-crosslinking agent, or the like.

In a case where the particulate water-absorbing agent satisfies the above condition, a disposable diaper produced with use of the particulate water-absorbing agent has an excellent ability to absorb urine from pulp and can have a reduced re-wet. This makes it possible to prevent skin irritation, rash and urine leakage.

(5-11) Bulk Specific Gravity

The particulate water-absorbing agent of the present invention has a bulk specific gravity of 0.57 g/cm$^3$ to 0.75 g/cm$^3$, preferably 0.58 g/cm$^3$ to 0.74 g/cm$^3$, more preferably 0.59 g/cm$^3$ to 0.73 g/cm$^3$, and even more preferably 0.60 g/cm$^3$ to 0.72 g/cm$^3$.

(5-12) Value of Diffusing Absorbency Under Pressure after 10 Minutes (DAP10min)

The particulate water-absorbing agent in accordance with the present invention has a value of diffusing absorbency under pressure after 10 minutes of 12.0 g/g or more, more preferably 14.0 g/g or more, even more preferably 16.0 g/g or more, and most preferably 18.0 g/g or more. Typically, a water-absorbing agent subjected to a surface cross-linking treatment has a value of diffusing absorbency under pressure after 10 minutes of 7 g/g or more. However, some water-absorbing agents, though not common, have a small value of diffusing absorbency under pressure after 10 minutes. A particulate water-absorbing agent having a small value of diffusing absorbency under pressure after 10 minutes has a degraded diffusion property in an absorbent body and may be unable to exhibit sufficient performance as an absorbent body, despite having an excellent DRC or an excellent DRC index. An upper limit of the value of the diffusing absorbency under pressure after 10 minutes is not particularly limited but is typically approximately 30 g/g or less.

(5-13) Yellowness (YI Value/Yellow Index)

Yellowness (YI value/Yellow Index, see European Patent No. 942014 and European Patent No. 1108745) is preferably 0 to 17, more preferably 0 to 16, even more preferably 0 to 15, and most preferably 0 to 14. The particulate water-absorbing agent preferably has little yellowing. Examples of a method of measurement of color encompass the method disclosed in International Publication No. WO 2009/005114 (method of measuring Lab value, YI value, WB value, and the like).

Causing the particulate water-absorbing agent to satisfy the conditions above makes it possible, when the particulate water-absorbing agent is used in combination with white pulp and a hygienic material, to produce a disposable diaper which does not cause a user to have a feeling of a foreign body due to coloration.

According to a preferred embodiment, after a colorations acceleration test (maintained for 1 week at 70° C. and 65 RH %), the particulate water-absorbing agent of the present invention has a YI value of 35 or less, preferably 30 or less, more preferably 25 or less, and even more preferably 22 or less. Causing the particulate water-absorbing agent to satisfy the conditions above makes it possible, when the particulate water-absorbing agent is used in combination with white pulp and a hygienic material, to produce a disposable diaper which does not cause a user to have a feeling of a foreign body due to coloration.

(5-14) Damage Resistance

According to a preferred embodiment, an amount of increase in generated particles having a particle diameter of 150 μm or less between before and after a damage resistance paint shaker test described in the Examples, in the particulate water-absorbing agent of the present invention, is +5% or less, preferably +4% or less, more preferably +3% or less, even more preferably +2% or less, and still even more preferably +1% or less.

(5-15) Amount of Dust

The content of the water-absorbing resin which is contained in the dust of the particulate water-absorbing agent of the present invention is 300 ppm or less, preferably 270 ppm or less, more preferably 240 ppm or less, and most preferably 200 ppm or less, with respect to a total amount of the particulate water-absorbing agent.

(5-16) Internal Gas Bubble Ratio

The particulate water-absorbing agent of the present invention has an internal gas bubble ratio of 0.5% to 2.5%, preferably 0.8% to 2.3%, more preferably 1.2% to 2.0%, and even more preferably 1.5% to 1.8%.

The present invention has been described with preferred embodiments for ease of understanding. The following description will discuss the present invention with reference to Examples. However, the above description and the Examples below are provided only for illustrative purposes, and are not provided for the purpose of limiting the present invention. Accordingly, the scope of the present invention is not limited to the embodiments or Examples specifically described in the present specification, but is limited only by the appended claims.

[Recap]

A method for measuring physical properties of a particulate water-absorbing agent in accordance with an aspect of the present invention and a particulate water-absorbing agent in accordance with an aspect of the present invention can be expressed as follows:

<1> A method for measuring an absorption speed of a particulate water-absorbing agent, including the step of: applying pressure to a portion of a bottom surface of a measurement container by use of a flat plate in a state in which part or whole of said particulate water-absorbing agent is fixed on the bottom surface of the measurement container, the bottom surface being surrounded by a frame, introducing an aqueous solution through an injection inlet with which the flat plate is equipped, and then measuring the amount of time elapsed until an end of absorption of the introduced aqueous solution by said particulate water-absorbing agent.

<2> A method for measuring an absorption speed of a particulate water-absorbing agent, including the steps of: applying pressure to a portion of a bottom surface of a measurement container by use of a flat plate in a state in which part or whole of said particulate water-absorbing agent is fixed on the bottom surface of the measurement container, the bottom surface being surrounded by a frame, introducing an aqueous solution through an injection inlet with which the flat plate is equipped, so that the introduced aqueous solution is absorbed by said particulate water-absorbing agent; and removing the flat plate after an elapse of a predetermined period of time since the aqueous solution has been introduced, placing a member capable of absorbing the aqueous solution on a top of said particulate water-absorbing agent, applying pressure for a predetermined time period, and measuring a mass of a portion of the aqueous solution, the portion being a portion absorbed by the member, to measure a re-wet of a liquid from said particulate water-absorbing agent.

<3> The method described in <1> or <2>, wherein an aspect ratio when the measurement container is viewed from above is 1:1.5 to 1:10.

<4> The method described in any one of <1> to <3>, wherein said particulate water-absorbing agent is dispersed uniformly on the bottom surface of the measurement container.

<5> The method described in any one of <1> to <4>, wherein the amount of said particulate water-absorbing agent dispersed with respect to an area of the bottom surface of the measurement container is 50 g/m² to 1000 g/m².

<6> The method described in any one of <1> to <5>, wherein a pressure condition (load) at the introduction of the aqueous solution is 0.2 kPa to 10.0 kPa.

<7> The method described in any one of <1> to <6>, wherein an area of the portion to which pressure is applied by the flat plate is 10% to 90% of an area of the bottom surface of the measurement container.

<8> The method described in any one of <1> to <7>, wherein the aqueous solution is introduced a plurality of times.

<9> The method described in any one of <1> to <8>, wherein a total amount of the aqueous solution introduced is 10 ml to 60 ml with respect to 1 g of said particulate water-absorbing agent.

<10> The method described in any one of <1> to <9>, wherein a sheet is placed between the flat plate and said particulate water-absorbing agent, the sheet having voids of a size that allows the aqueous solution to pass therethrough but does not allow said particulate water-absorbing agent to pass therethrough.

<11> A particulate water-absorbing agent having the following physical properties (1) and (2):

(1) a centrifuge retention capacity (CRC) of 30 g/g to 50 g/g; and (2) an absorbent performance index (API) of 150 or less, the absorbent performance index (API) being expressed by the following formula:

Absorbent performance index (API)=First absorption time [sec]×Second absorption time [sec]×Third absorption time [sec]×Re-wet [g]/1000.

<12> The particulate water-absorbing agent described in <11>, wherein the absorbent performance index (API) is 100 or less.

<13> A particulate water-absorbing agent having the following physical properties (1) and (2):

(1) a centrifuge retention capacity (CRC) of 30 g/g to 50 g/g; and (2) a new absorbent performance index (nAPI) of 240 or less, the new absorbent performance index (nAPI) being expressed by the following formula:

New absorbent performance index (nAPI)=Second absorption time [sec]×Third absorption time [sec]×Re-wet [g]/10.

<14> The particulate water-absorbing agent described in <13>, wherein the new absorbent performance index (nAPI) is 190 or less.

<15> The particulate water-absorbing agent described in any one of <11> to <14>, further having the following physical properties (3) to (5):

(3) a value of diffusing absorbency under pressure after 10 minutes (DAP10min) of 12.0 g/g or more;

(4) a gel permeation rate (GPR) of 25 g/min or more; and (5) a content of a water-absorbing resin contained in a dust of said particulate water-absorbing agent of 300 ppm or less, with respect to a total amount of said particulate water-absorbing agent.

<16> The particulate water-absorbing agent described in any one of <11> to <15>, wherein said particulate water-absorbing agent has a surface tension of 65 mN/m or more.

<17> The particulate water-absorbing agent described in any one of <11> to <16>, wherein an index of DRC defined by the following Formula 1 is 43 or less, Index of DRC=(49−DRC5 min)/(D50/1000)    Formula 1.

<18> The particulate water-absorbing agent described in <17>, wherein the index of DRC is 30 or less.

<19> The particulate water-absorbing agent described in <17>, wherein the index of DRC is 20 or less.

<20> The particulate water-absorbing agent described in any one of <11> to <19>, wherein particles of said particulate water-absorbing agent have a non-uniformly pulverized particle shape.

<21> The particulate water-absorbing agent described in any one of <11> to <20>, wherein a moisture absorption fluidity (B.R.) is 50 mass % or less.

<22> The particulate water-absorbing agent described in any one of <11> to <21>, wherein a degradable soluble content is 30 mass % or less.

<23> The particulate water-absorbing agent described in any one of <11> to <22>, wherein a fluid retention capacity under pressure (AAP) is 18 g/g or more.

<24> The particulate water-absorbing agent described in any one of <11> to <22>, wherein a fluid retention capacity under pressure (AAP) is 26 g/g or more.

<25> The particulate water-absorbing agent described in any one of <11> to <24>, wherein an internal gas bubble ratio defined by the following formula is 0.5% to 2.5%, Internal gas bubble ratio [%]={(true density [g/cm$^3$]−apparent density [g/cm$^3$])/true density [g/cm$^3$]}×100.

<26> The particulate water-absorbing agent described in any one of <11> to <25>, wherein a bulk specific gravity is 0.57 to 0.75 [g/cm$^3$].

<27> The particulate water-absorbing agent described in any one of <11> to <26>, wherein a value of diffusing absorbency under pressure after 10 minutes (DAP10min) is 18.0 g/g or more.

<28> An absorbent body including a particulate water-absorbing agent described in any one of <11> to <27>.

<29> An absorbent article including an absorbent body described in <28>.

EXAMPLES

The following description will discuss the present invention in greater detail on the basis of Examples and Comparative Example. Note, however, that the present invention is not limited to the description thereof and that any Example derived from a proper combination of technical means disclosed in respective different Examples is also encompassed in the scope of the present invention.

Electric devices/apparatuses (including devices/apparatuses used to measure physical properties of a particulate water-absorbing agent) in Examples and Comparative Example each used a 200-V or 100-V electric power supply, unless otherwise specified. Further, the physical properties of a particulate water-absorbing agent of the present invention were measured at room temperature (20° C. to 25° C.) and at a relative humidity of 50% RH, unless otherwise specified.

[Measurements of Physical Properties of Particulate Water-Absorbing Agent or Water-Absorbing Resin]

(a) Centrifuge Retention Capacity (CRC)

The centrifuge retention capacity (fluid retention capacity without pressure, CRC) of the particulate water-absorbing agent or the water-absorbing resin of the present invention was measured in conformity with an EDANA method (ERT 441.2-02).

(b) Fluid Retention Capacity Under Pressure (AAP)

The fluid retention capacity under pressure (AAP) of the particulate water-absorbing agent or the water-absorbing resin of the present invention was measured in conformity with an EDANA method (ERT 441.2-02).

(c) Moisture Content

The moisture content of the particulate water-absorbing agent or the water-absorbing resin of the present invention was measured in conformity with an EDANA method (ERT430.2-02). Note that for the present invention, in measurements of the moisture content of the particulate water-absorbing agent (sample) or the water-absorbing resin (sample), the amount of the sample was changed to 1.0 g, and the drying temperature was changed to 180° C.

Further, in measurements of the moisture content of a hydrogel having a relatively high water content (moisture content of 20 mass % or more), a drying time was changed to 24 hours.

(d) Dunk Retention Capacity 5 Minutes (Dunk Retention Capacity (DRC5 Min))

Figure 4:
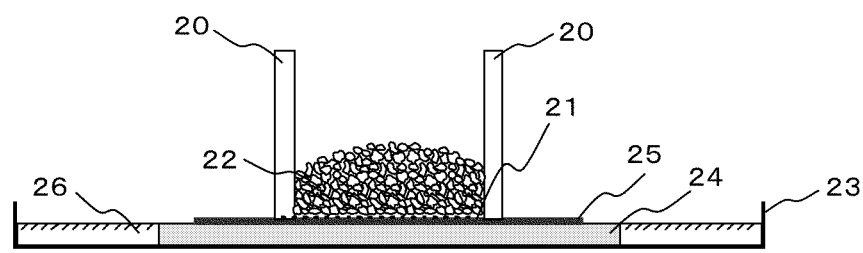
FIG. 4 is a cross-sectional view schematically illustrating a measurement device for use in measurement of a dunk retention capacity (DRC).

A device illustrated in FIG. 4 was used. In the device, a 400-mesh metal gauze 21 made of stainless steel (having a mesh size of 38 μm) was fused to the bottom of a plastic supporting cylinder 20 having an inner diameter of 60 mm. Then, 1.000 g±0.005 g of the particulate water-absorbing agent or a water-absorbing resin was dispersed uniformly on the metal gauze, at room temperature (20° C. to 25° C.) and at a humidity of 50% RH. Then, the mass Wa (g) of this measuring device as a whole was measured.

A glass filter 24 having a diameter of 120 mm (manufactured by Sougo Rikagaku Glass Seisakusho Co., Ltd., fine pore diameter: 100 μm to 120 μm) was placed in a petri dish 23 having a circular or square shape whose bottom area was 400 cm$^2$. Then, 0.90-mass % aqueous sodium chloride solution 26 (23° C.±0.5° C.) was added in such an amount that the level of the 0.90-mass % aqueous sodium chloride solution 26 was equal to the upper surface of the glass filter 24 (a state in which liquid was slightly bulging due to its surface tension at the outer periphery of the glass filter or a state in which approximately 50% of the surface of the glass filter was covered by the liquid). On the aqueous sodium chloride solution 26 and the glass filter 24, a sheet of filter paper 25 having a diameter of 110 mm (available from Advantec Toyo Kaisha, Ltd., product name: JIS P 3801 No. 2, with a thickness of 0.26 mm and a retaining particle diameter of 5 μm) was placed in such a manner that the entire surface of the sheet of filter paper 25 was wet.

A whole of the measuring device described above was placed on the wet filter paper 25 so that the water-absorbing resin absorbed the liquid and then turned into a swollen gel 22 (the temperature of the liquid was precisely controlled at 23° C.±0.5° C. during measurement). After a lapse of exactly 5 minutes (300 seconds), the whole measuring device was lifted up and the mass Wb (g) of the whole measuring device was measured. Then, DRC5 min (g/g) was calculated from Wa and Wb by the following Formula d-1:

DRC5 min (g/g)={(Wb−Wa)/(mass of particulate water-absorbing agent or water-absorbing resin)}    Formula d-1

(e) Surface Tension

Into a 100 ml beaker which had been sufficiently washed, 50 ml of 0.90-mass % aqueous sodium chloride solution, which had been adjusted to 20° C., was put. Then, the surface tension of the aqueous sodium chloride solution was measured with use of a surface tension meter (manufactured by KRUSS, K11 automatic surface tension meter). In this measurement, the surface tension needs to fall within a range of 71 mN/m to 75 mN/m.

Next, a fluorine resin rotor, which had been sufficiently washed and had a length of 25 mm, and 0.5 g of the particulate water-absorbing agent or the water-absorbing resin were put in the beaker containing the 0.90-mass % aqueous sodium chloride solution whose temperature had been adjusted to 20° C. and whose surface tension had been measured. Then, a resultant solution was stirred at 500 rpm for 4 minutes. After 4 minutes elapsed, the stirring was stopped. Thereafter, after sedimentation of the particulate water-absorbing agent or the water-absorbing resin which had absorbed water, the surface tension of a supernatant liquid was measured with similar procedures. Note that, in the present invention, a plate method using a platinum plate was employed, and the plate was sufficiently washed with deionized water and also cleaned with heat by the use of a gas burner before being used in each of the above measurements.

(f) Particle Size Distribution (PSD) and Logarithmic Standard Deviation (σξ) of Particle Size Distribution The particle size distribution (PSD) and the logarithmic standard deviation (σξ) of particle size distribution of the particulate water-absorbing agent in accordance with the present invention were measured in conformity with a measuring method disclosed in U.S. Patent Application Publication No. 2006/204755.

That is, 10.00 g of the particulate water-absorbing agent was classified by using JIS standard sieves (The IIDA TESTING SIEVE: 80 mm in inner diameter; JIS Z8801-1 (2000)) having respective mesh sizes of 850 μm, 710 μm, 600 μm, 500 μm, 425 μm, 300 μm, 212 μm, 150 μm, 106 μm, and 75 μm or sieves corresponding to the JIS standard sieves. After this classification, the mass of each sieve was measured, and the mass percentage (mass %) of particles having a particle diameter of less than 150 μm was calculated. Note that the "mass percentage of particles having a particle diameter of less than 150 μm" refers to a mass proportion (%) of particles capable of passing through a JIS standard sieve having a mesh size of less than 150 μm, relative to a whole of the particulate water-absorbing agent.

Further, a graph of a residual percentage R of each particle size mentioned above was plotted on a logarithmic probability paper, and a particle diameter corresponding to R=50 mass % was read as the mass average particle diameter (D50) from the graph. Note that the mass average particle diameter (D50) refers to a particle diameter corresponding to 50 mass % of the whole of the particulate water-absorbing agent. Furthermore, note that the logarithmic standard deviation (σξ) of the particle size distribution is expressed by the following Formula f-1 and that a smaller value of the logarithmic standard deviation (σξ) of the particle size distribution indicates a narrower particle size distribution.

$$\sigma\xi = 0.5 \times \ln(X2/X1) \quad \text{Formula f-1}$$

where X1 represents a particle diameter when R=84.1%, and X2 represents a particle diameter when R=15.9%.

(g) Moisture Absorption Fluidity (Moisture Adsorption Blocking Ratio) (B.R.; Blocking Ratio)

On an aluminum cup having a diameter of 52 mm, 2 g of the particulate water-absorbing agent or the water-absorbing resin was uniformly dispersed and then left to stand still for one hour in a thermo-hygrostat (PLATINOUSLUCIFERPL-2G; manufactured by Tabai Espec Corp.) at a temperature of 25° C. and at a relative humidity of 90% RH±5% RH. After one hour elapsed, the particulate water-absorbing agent or the water-absorbing resin in the aluminum cup was calmly transferred onto a JIS standard sieve (The IIDA TESTING SIEVE: 80 mm in inner diameter) having a mesh size of 2000 μm (JIS 8.6 mesh). The particulate water-absorbing agent or the water-absorbing resin was then classified at room temperature (20° C. to 25° C.) and at a relative humidity of 50% RH for 5 seconds, by using a Ro-Tap sieve shaker (ES-65 sieve shaker manufactured by Sieve Factory Iida Co., Ltd.; whose rotation speed was 230 rpm and number of impacts was 130 rpm). Thereafter, the mass (W1 [g]) of the particulate water-absorbing agent or the water-absorbing resin remaining on the JIS standard sieve and the mass (W2 [g]) of the particulate water-absorbing agent or the water-absorbing resin which had passed through the sieve were measured. Subsequently, the moisture absorption fluidity (moisture adsorption blocking ratio) was calculated by the following Formula g-1. Note that a lower value of the blocking ratio means a better moisture absorption fluidity.

$$\text{Moisture absorption fluidity } (B.R.) \text{ (mass \%)} = \{W1/(W1+W2)\} \times 100 \quad \text{Formula g-1}$$

(h) Degradable Soluble Content

In a 250 ml plastic container in which a 35 mm rotor was placed and which had inner and outer lids, 200.0 g of an aqueous solution containing 0.05 mass % of L-ascorbic acid and 0.90 mass % of sodium chloride (degradation test liquid/mixture of 0.10 g of L-ascorbic acid and 199.90 g of 0.90 mass % aqueous sodium chloride solution) was weighed and taken. Then, 1.00 g of the particulate water-absorbing agent or the water-absorbing resin was added to the aqueous solution, and the plastic container was sealed with the inner and outer lids. Thereafter, the plastic container was left to stand still for 2 hours, in a thermostat which had been adjusted to 60° C.±2° C. After 2 hours elapsed, the plastic container was taken out from the thermostat and one-hour stirring using a stirrer (rotation speed: 500 rpm) was carried out at room temperature. A water-soluble content of the particulate water-absorbing agent or the water-absorbing resin was extracted by the above operation.

After the stirring, the extraction liquid was filtered with the use of a sheet of filter paper (manufactured by Advantec Toyo Kaisha, Ltd., product name: JIS P 3801 No. 2, with a thickness of 0.26 mm and a retaining particle diameter of 5 μm). Then, 50.0 g of a filtrate thus obtained was used as a liquid for measurement. Next, the liquid for measurement was titrated with a 0.1 N NaOH aqueous solution until the liquid had a pH of 10, and then titrated with a 0.1 N HCl aqueous solution until the liquid had a pH of 2.7. Respective titers in the above titration were determined as [NaOH] mL and [HCl] mL.

Further, similar operations were carried out on 200.0 g of only the degradation test liquid to which neither the particulate water-absorbing agent nor the water-absorbing resin was added, and blank titers ([b2NaOH] mL and [b2HCl] mL) were determined.

Subsequently, the degradable soluble content was calculated according to the following Formula h-1 from the above titers and a monomer average molecular weight.

$$\text{Degradable soluble content (mass \%)} = 0.1 \times \text{monomer average molecular weight} \times 200 \times 100 \times ([HCl] - [b2HCl])/1000/1.0/50.0 \quad \text{Formula h-1}$$

Note that in a case where the monomer average molecular weight was unknown, the monomer average molecular weight was calculated by using a neutralization rate calculated by the following Formula h-2.

$$\text{Neutralization rate[mol \%]} = \{1 - ([NaOH] - [b1NaOH])/([HCl] - [b1HCl])\} \times 100 \quad \text{Formula h-2}$$

(i) Bulk Specific Gravity

The term "Density" (ERT 460.2-02) refers to the bulk specific gravity of a water-absorbing agent. Note that the bulk specific gravity was measured in conformity with JIS K3362, with reference to ERT 460.2-02, in the present invention.

The bulk specific gravity was measured by use of a bulk specific gravity measuring device (manufactured by Kuramochi Scientific Instrument Seisakusho) in conformity with JIS K 3362. After 100.0 g of the water-absorbing agent, which had been sufficiently stirred so as to avoid deviation of particle size, was placed in a funnel whose damper was closed, the damper was opened quickly so that the water-absorbing agent was dropped into a receiver having an internal capacity of 100 ml. Note that the weight (unit: g) of the receiver (this weight is referred to as "mass W9") was weighed in advance.

After part of the water-absorbing agent, which part was protruding from the top of the receiver, was removed by use of a glass rod, the weight (unit: g) of the receiver containing the water-absorbing agent (this weight is referred to as "mass W10") was accurately measured to the unit of 0.1 g, and the bulk specific gravity was calculated by the following Formula i-1.

$$\text{Bulk specific gravity (g/cm}^3\text{)}=(W10-W9)/100 \quad \text{Formula i-1}$$

Note that the above measurement was carried out at an ambient temperature of 24.2° C. and at a relative humidity of 43% RH.

(j) Increase in Fine Powder from Before to after Damage (Damage Resistance)

An increase in fine powder (amount of increase in particles which pass through a 150 μm mesh) from before to after damage to the particulate water-absorbing agent of the present invention, which increase in fine powder is defined by a measuring method described later, is preferably 4 mass % or less, and more preferably 3.5 mass % or less. The particulate water-absorbing agent having the increase in fine powder in the above range causes no problem of deterioration of physical properties in actual use for diaper production, etc.

<Increase in Fine Powder after Damaging>

A paint shaker test described below was carried out on the water-absorbing agent. An amount of increase in particles having a particle diameter of 150 μm or less from before to after the paint shaker test was measured by classification of the water-absorbing agent with use of a JIS standard sieve having a mesh size of 150 μm.

[Paint Shaker Test]

A paint shaker test (PS-test) is a test in which 10 g of glass beads having a diameter of 6 mm and 30 g of a water-absorbing resin are put in a glass container having a diameter of 6 cm and a height of 11 cm and then the glass container is attached to a paint shaker (Toyo Seiki Seisaku-sho, Ltd., product No. 488) and is shaken at 800 cycles/min (CPM) for 30 minutes. The details of a device for the paint shaker test are disclosed in Japanese Patent Application Publication, *Tokukaihei*, No. 9-235378.

After the glass container is shaken, the glass beads are removed with use of a JIS standard sieve having a mesh size of 2 mm, so that a damaged water-absorbing resin is obtained.

(k) Water-Soluble Content (Ext)

The water-soluble content (Ext) of the particulate water-absorbing agent of the present invention was measured in conformity with an EDANA method (ERT470.2-02).

(l) Measurement of Value of Diffusing Absorbency Under Pressure after 10 Minutes (DAP10min)

A value of diffusing absorbency under pressure after 10 minutes of a particulate water-absorbing agent was measured according to a measuring method disclosed in Japanese Patent Application Publication, *Tokukai*, No. 2010-142808. Specifically, the value of diffusing absorbency under pressure after 10 minutes of the particulate water-absorbing agent was measured as below.

First, a measuring device used to measure the diffusing absorbency under pressure will be briefly described below with reference to FIGS. 6 to 8.

Figure 6:
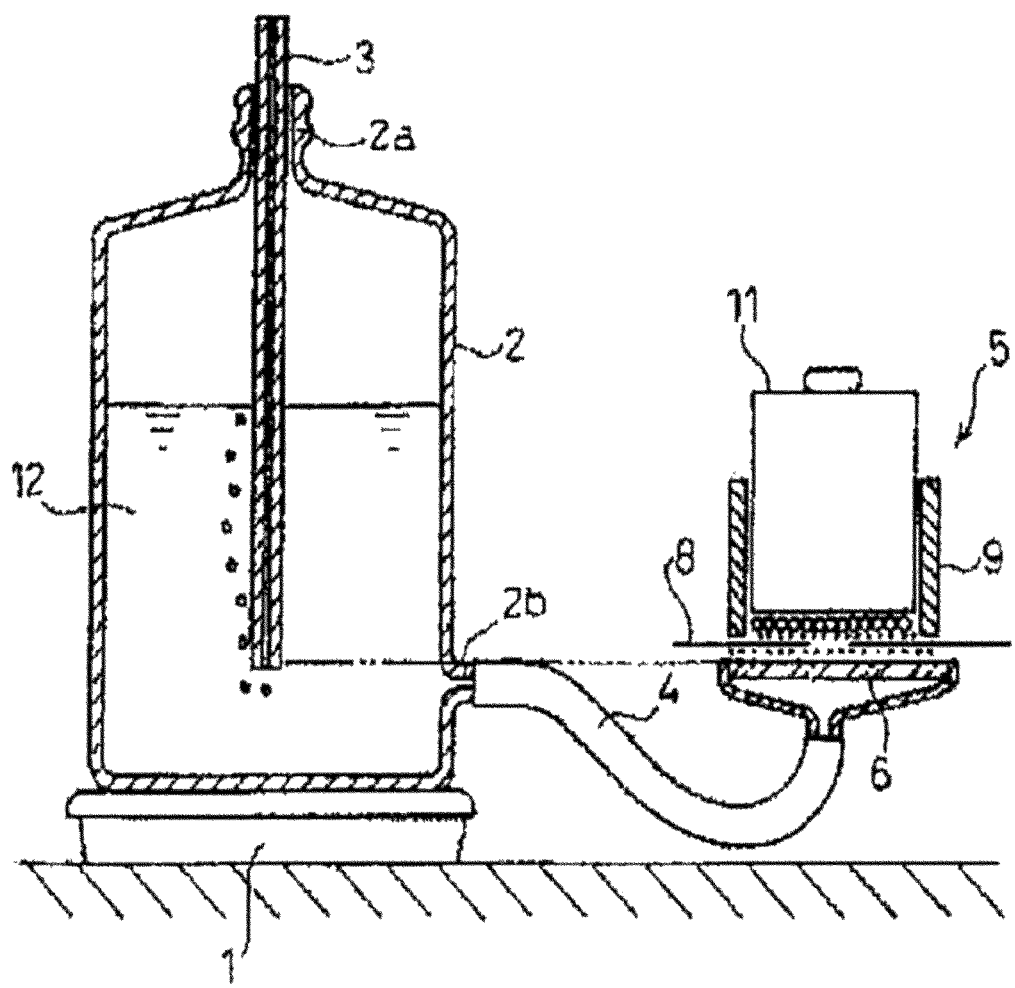
FIG. 6 is a cross-sectional view schematically illustrating a measurement device for use in measurement of a diffusing absorbency (DAP).

As illustrated in FIG. 6, the measuring device includes: a balance 1; a container 2 which is placed on the balance 1 and which has a given capacity; an external air intake pipe 3; a duct 4; a glass filter 6; and a measuring section 5 which is placed on the glass filter 6. The container 2 has an opening 2a in its top, and has an opening 2b in its side surface. The external air intake pipe 3 is fitted into the opening 2a, and the duct 4 is attached to the opening 2b. A certain amount of 0.90 mass % aqueous sodium chloride solution 12 is put in the container 2. A lower end of the external air intake pipe 3 is immersed in the 0.90 mass % aqueous sodium chloride solution 12. The glass filter 6 is formed so as to have a diameter of 70 mm. The container 2 and the glass filter 6 are communicated with each other via the duct 4. The glass filter 6 is fixed so that an upper surface of the glass filter 6 is located at a position slightly higher than a position of the lower end of the external air intake pipe 3.

Figure 7:
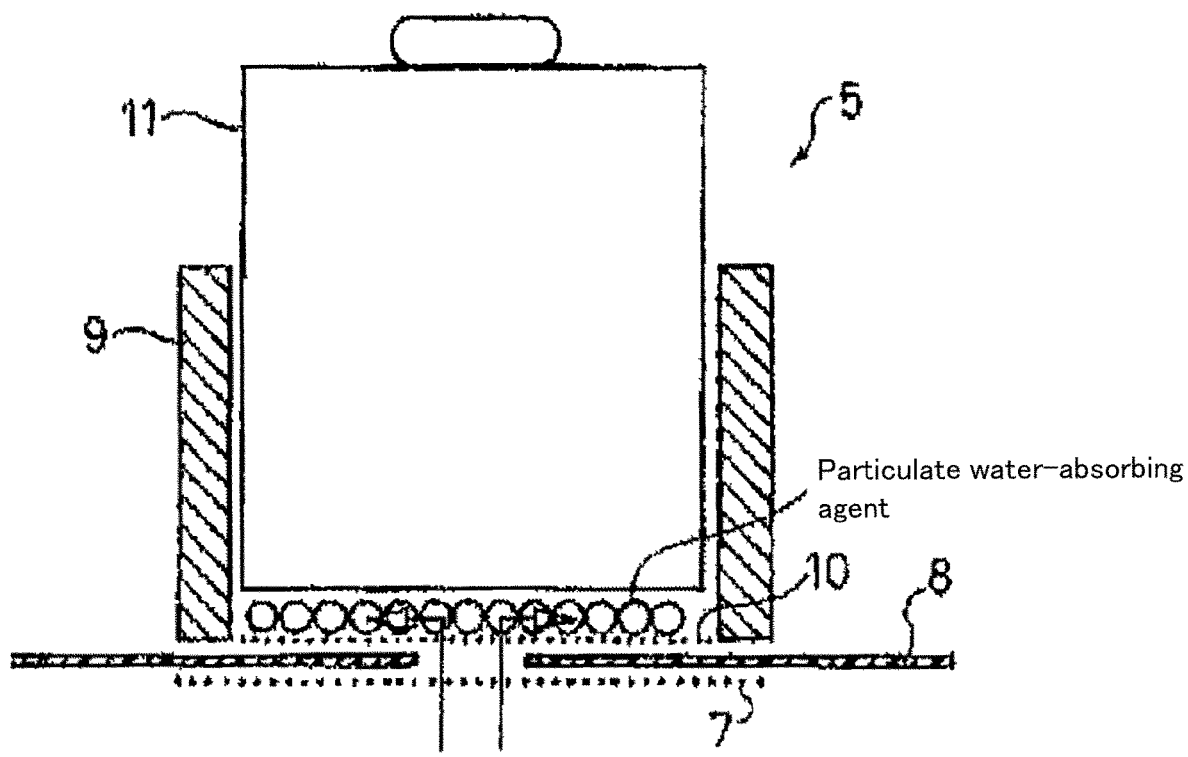
FIG. 7 is a cross-sectional view illustrating main components of the measurement device illustrated in FIG. 6.
Figure 8:
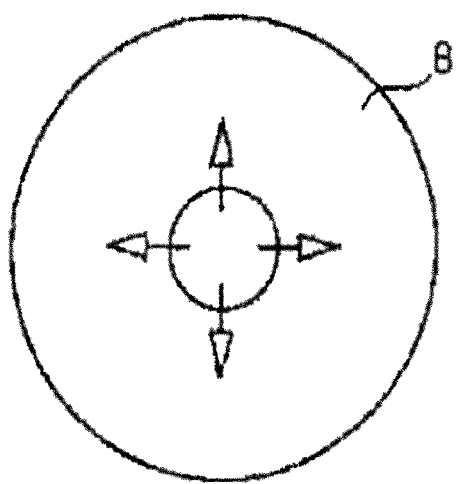
FIG. 8 is a plan view schematically illustrating directions in which a 0.90 mass % aqueous sodium chloride solution diffuses in the measurement device illustrated in FIG. 6.

As illustrated in FIG. 7, the measuring section 5 includes a filter paper 7, a sheet 8, a supporting cylinder 9, a metal gauze 10 attached to a bottom of the supporting cylinder 9, and a weight 11. The measuring section 5 is configured such that the filter paper 7, the sheet 8, and the supporting cylinder 9 (that is, the metal gauze 10) are placed in this order on the glass filter 6 and that the weight 11 is placed inside the supporting cylinder 9, that is, on the metal gauze 10. The sheet 8 is made of polyethylene terephthalate (PET). The sheet 8 is formed in a ring shape so as to have, in its middle part, an opening having a diameter of 18 mm, and has a thickness of 0.1 mm. The supporting cylinder 9 is formed so as to have an inner diameter of 60 mm. The metal gauze 10 is made of stainless steel, and is a 400-mesh metal gauze (having a mesh size of 38 μm) according to a JIS standard. The metal gauze 10 is configured such that a certain amount of a particulate water-absorbing agent is uniformly spread on the metal gauze 10. A mass of the weight 11 is adjusted so that the weight 11 can uniformly apply a load of 20 g/cm² (1.96 kPa) to the metal gauze 10, that is, the particulate water-absorbing agent.

The value of diffusing absorbency under pressure after 10 minutes was measured with use of the measuring device thus configured. The measuring method will be described below.

First, given preparation was made. For example, a certain amount of the 0.90 mass % aqueous sodium chloride solution 12 was put in the container 2, and the external air intake pipe 3 was fitted into the container 2. Next, the filter paper 7 was placed on the glass filter 6. The sheet 8 was placed on the filter paper 7 so that the opening of the sheet 8 was located in a middle part of the glass filter 6. In parallel to those placing operations, 1.5 g of a particulate water-absorbing agent was uniformly spread inside the supporting cylinder 9, that is, on the metal gauze 10. The weight 11 was placed on the particulate water-absorbing agent.

Next, the metal gauze 10, that is, the supporting cylinder 9 inside which the particulate water-absorbing agent and the weight 11 were placed was placed on the sheet 8 so that a middle part of the metal gauze 10 matched the middle part of the glass filter 6.

Subsequently, the particulate water-absorbing agent was caused to absorb the 0.90 mass % aqueous sodium chloride solution 12 over 10 minutes from a time point when the supporting cylinder 9 was placed on the sheet 8. A mass W2 (g) of the 0.90 mass % aqueous sodium chloride solution 12 thus absorbed was measured with use of the balance 1. Note that, as illustrated in FIGS. 7 and 8, the 0.90 mass % aqueous sodium chloride solution 12 passed through the opening of the sheet 8 and was then absorbed by the particulate water-absorbing agent while the 0.90 mass % aqueous sodium chloride solution 12 was substantially uniformly diffusing in a horizontal direction (shown by an arrow in FIG. 8) of the particulate water-absorbing agent.

Thereafter, a diffusing absorbency under pressure (value after 10 minutes) (g/g) after 10 minutes elapsed from start of absorption was calculated from the above mass W2 by the following Formula l-1.

Diffusing absorbency under pressure (g/g)=$W2$/mass of a particulate water-absorbing agent    Formula l-1

(m) Content of Water-Absorbing Resin in Dust

Content of water-absorbing resin in dust (content of water-absorbing resin in dust occurring from 100 parts by mass of particulate water-absorbing agent) was determined through the following procedure:
Step 1: Measure amount of dust.
Step 2: Determine proportions (% by mass) of water-absorbing resin, $SiO_2$, and aluminum sulfate contained in dust. In a case where $SiO_2$ and/or aluminum sulfate is/are not contained in the dust, the proportion thereof is considered to be 0% by mass. Step 3: Calculate content of the water-absorbing resin in the dust.

<Measurement of Amount of Dust>

An increase in mass due to dust attracted and caught by glass fiber filter paper over a predetermined period of time was measured in accordance with the conditions described below. This measured value was considered to be the amount of dust occurring from the particulate water-absorbing agent. The measuring apparatus used was Heubach DUSTMETER (manufactured by Heubach Engineering GmbH (Germany)), and a measurement mode Type I was used. The measurement was carried out in an atmosphere at a temperature of 25° C. (±2° C.) and at a relative humidity of 20% to 40%. The measurement was carried out under a normal pressure.

Specifics of the measurement method are as follows.
1. The particulate water-absorbing agent (100.00 g) was placed as a measurement sample into a rotatable drum of the DUSTMETER.
2. A mass ([Da] g) of the glass fiber paper filter was measured to 0.00001 g accuracy. The glass fiber filter paper retains a particle diameter of 0.5 μm (can be determined in accordance with precipitation retaining properties defined in JIS P3801) and has a diameter of 50 mm. For example, the glass fiber filter paper may be a glass fiber filter paper into which the product GLASS FIBER, GC-90 (manufactured by ADVANTEC), or an equivalent product, is processed to have a diameter of 50 mm.
3. A coarse particle separator was fixed to the rotatable drum, and a filter case to which the glass fiber filter paper was mounted was fixed to the coarse particle separator.
4. The DUSTMETER was set to the following measurement conditions, and then measurement was carried out. Rotation speed of the drum: 30 R/min; suction air volume: 20 L/min; time (measurement time): 30 minutes.
5. After the 30 minutes elapsed, a mass ([Db] g) of the glass fiber filter paper was measured to 0.00001 g accuracy.

The amount of dust was calculated from [Da] and [Db] by following Formula m-1. Calculated by the following Formula m-1 is the amount (unit: ppm) of dust with respect to the total mass of the particulate water-absorbing agent.

Amount of dust (ppm)={([$Db$]−[$Da$])/100.00}× 1000000    Formula m-1

<Determination of Proportions (% by Mass) of Water-Absorbing Resin, $SiO_2$, and Aluminum Sulfate in Dust>

The proportions (% by mass) of water-absorbing resin, $SiO_2$, and aluminum sulfate in the dust (collected in the above-described dust amount measurement) were determined.

In order to determine these proportions, the proportions of elemental Na, elemental Si, and elemental Al contained in the dust were analyzed. Then, the mass ratio of the water-absorbing resin, the $SiO_2$, and the aluminum sulfate was calculated from results of the analysis, in accordance with the neutralization rate and the mass average molecular weight of the water-absorbing resin (including sodium salt as a neutralized salt).

Note that even in a case where the neutralized salt of the water-absorbing resin is not sodium salt but some other salt such as potassium salt, lithium salt, or ammonium salt, it is possible to find the proportions of water-absorbing resin, $SiO_2$, and aluminum sulfate in the dust in a manner similar to the above-described method. For example, in a case where the neutralized salt of the water-absorbing resin is potassium salt, analysis can be performed to determine proportions of elemental K, elemental Si, and elemental Al. Even in a case where the water-absorbing resin contains other substance (e.g., water and water-insoluble inorganic fine particles other than $SiO_2$), measurement can be made as necessary.

Quantitative analysis of the elemental Na, elemental Si, and elemental Al contained in the dust was carried out via a ZAF method with use of an SEM/EDS (Energy Dispersive X-ray Spectrometer).

An appropriate amount of dust was collected from the glass fiber filter paper used in the above-described dust amount measurement and then subjected to the quantitative analysis. The dust was transferred to a stage for SEM, on which was affixed carbon tape measuring 5 mm×5 mm. At this time, the dust was dispersed uniformly on the carbon tape.

Measurement conditions used during the quantitative analysis are as follows.
Device: Scanning electron microscope (JSM-5410LV SCANNING MICROSCOPE, manufactured by JEOL)
Acceleration voltage: 20 kV
Magnification: 20 times
Measurement field of view: Approximately 900 μm×1200 μm (measurement carried out in state where at least 50% by area of the entire area of the measurement field of view was covered by dust)
Si peak: SiKα 1.739 KeV
Na peak: NaKα 1.041 KeV
Al peak: AlKα 1.486 KeV Note that in cases where the above-described peaks of elements of interest coincided with the peak of some other element (for example, NaKα vs ZnLα), measured values were calibrated by subtracting the value of the peak derived from the other element (ZnKα in the case of Zn).

By using the % by mass of the elemental Na (hereinafter abbreviated as "Na %"), the % by mass of the elemental Al (hereinafter abbreviated as "Al %"), the % by mass of the elemental Si (hereinafter abbreviated as "Si %"), the neutralization rate N (mol %) (described below) of the water-absorbing resin, and the polymer unit mass average molecular weight Mw (described below) of the water-absorbing resin, the proportions (% by mass) of the water-absorbing resin, the $SiO_2$, and the aluminum sulfate contained in the dust can be calculated from Formulas m-2 to m-8 below.

Polymer unit mass average molecular weight
$Mw$=72.06×(1−$N$/100)+94.05×$N$/100    Formula m-2

Water-absorbing resin component amount $P$={($Na$%/23)/($N$/100)}×Mw    Formula m-3

$SiO_2$ component amount $S$=($SP$/0/28.08)×60.08    Formula m-4

Aluminum sulfate component amount $A=(Al/O/26.98)\times 630.4/2$   Formula m-5

Proportion (% by mass) of water-absorbing resin in dust=$\{P/(P+S+A)\}\times 100$   Formula m-6 proportion (% by mass) of $SiO_2$ in dust=$\{S/(P+S+A)\}\times 100$   Formula m-7

Proportion (% by mass) of aluminum sulfate in dust=$\{A/(P+S+A)\}\times 100$   Formula m-8

The neutralization rate N of the water-absorbing resin as used in the above formulas m-2 and m-3 can be determined in a manner as described earlier in the (Neutralization) section in "(3-1) Step of preparing aqueous monomer solution" or can be calculated by using the method described earlier in "(h) Degradable soluble content".

The proportions of the water-absorbing resin, the $SiO_2$, and the aluminum sulfate in the dust are preferably measured by the above-described method. However, in a case where, for example, the components are unknown or there are a large number of other elements existing in the dust, a conventionally known method (elemental analysis or the like) can be used to carry out measurement.

<Measurement of Content of Water-Absorbing Resin in Dust>

The content of the water-absorbing resin in the dust can be calculated by Formula m-9 below, using the amount of dust (collected in the above-described dust amount measurement) and the measured proportions of the water-absorbing resin, the $SiO_2$, and the aluminum sulfate. The value of the amount of dust as used in Formula m-9 below is a value with respect to the total amount of the particulate water-absorbing agent (the total mass of the water-absorbing resin composition), as described earlier. As such, in Formula m-9 below, the value of the content of the water-absorbing resin in the dust is also a value with respect to the total mass of the water-absorbing resin composition.

Content of water-absorbing resin in dust (ppm)= amount of dust×$P/(P+S+A)$   Formula m-9

(n) Gel Permeation Rate (GPR)

With reference to the saline flow conductivity (SFC) test described in the specification of U.S. Pat. No. 5,849,405, measurement conditions were changed, and the procedure as below was used.

Figure 5:
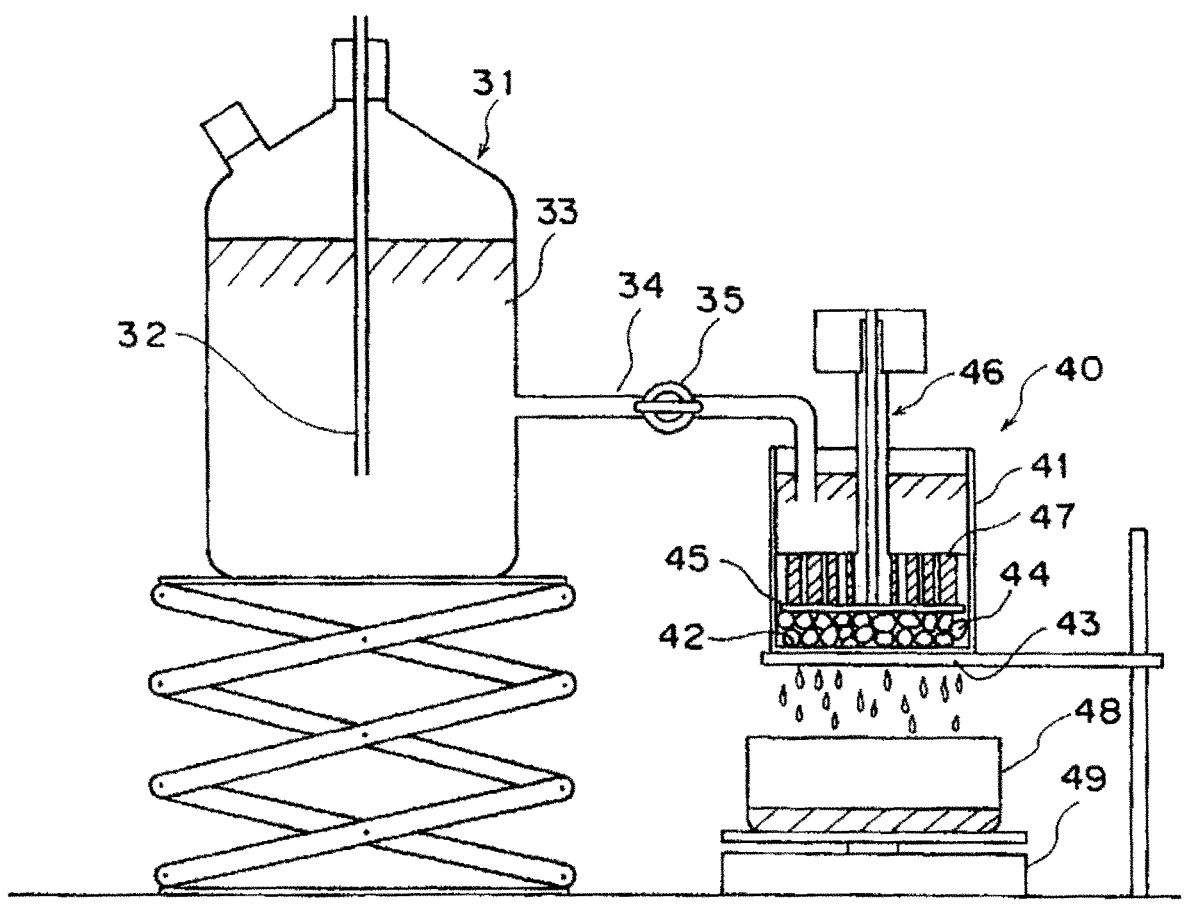
FIG. 5 is a cross-sectional view schematically illustrating a measurement device for use in measurement of a gel permeation rate (GPR).

With use of an apparatus illustrated in FIG. 5, a swollen gel 44 was obtained by causing 0.900 g of particulate water-absorbing agent placed uniformly in a container 40 to be swollen for 60 minutes without application of pressure in a 0.90 mass % aqueous sodium chloride solution. Next, a piston 46 was placed on the swollen gel 44, and, under a pressure of 0.3 psi (2.07 kPa), a 0.90 mass % aqueous sodium chloride solution 33 from a tank 31 was caused to pass through a swollen gel layer at a constant hydrostatic pressure (3923 dyne/cm$^2$). This GPR test was carried out at room temperature (20° C. to 25° C.). A computer and an even balance 49 were used for 3-minute recording of the amounts of liquids passing through the gel layer at intervals of 5 seconds as a function of time. An average of flow rates in a time period from a time after an elapse of one minute since the start of flow of the solution to a time after an elapse of three minutes since the start of flow of the solution was determined as a value of gel permeation rate (GPR) in units of g/min.

In the apparatus illustrated in FIG. 5, a glass tube 32 was inserted in the tank 31, and a lower end of the glass tube 32 was arranged such that the 0.90 mass % aqueous sodium chloride solution 33 was maintained at a height of 5 cm above from the bottom of the swollen gel 44 in a cell 41. The 0.90 mass % aqueous sodium chloride solution 33 in the tank 31 was supplied to the cell 41 through a cock-equipped L-shaped tube 34 equipped with a cock 35. Under the cell 41, a collection container 48 was disposed for collecting the solution which had passed through the gel layer. The collection container 48 was placed on the even balance 49. The inner diameter of the cell 41 was 6 cm, and a No. 400 metal gauze 42 made of stainless steel (mesh size of 38 μm) was placed on the bottom surface of the lower part. A lower part of the piston 46 had holes 47 of a sufficient size that allows the solution to pass through. At the bottom of the piston 46 was installed a No. 400 metal gauze 45 made of stainless steel (mesh size of 38 μm) which has excellent permeability that prevents the particulate water-absorbing agent or the swollen gel 44 thereof from entering the holes 47. The cell 41 was put on a stand to place the cell, and the surface of the stand in contact with the cell was set on the metal gauze 43 made of stainless steel that did not prevent the passage of the solution.

(o) Internal Gas Bubble Ratio

True density and apparent density of a particulate water-absorbing agent were measured by the method described below.

(o-1) Apparent Density

An apparent density of the water-absorbing resin from which water had been removed was measured by use of a dry densimeter (a volume of the water-absorbing resin having a predetermined mass was dry-measured). The apparent density is a density calculated in consideration of gas bubbles (internal gas bubbles) present inside a resin. The measurement method is as follows. Specifically, 6.0 g of the water-absorbing resin was weighed and placed in an aluminum cup whose bottom surface had a diameter of approximately 5 cm. Then, the water-absorbing resin was dried in a windless drier at 180° C. The water-absorbing resin was left to stand still for 3 hours or more until the moisture content of the water-absorbing resin was 1 mass % or less, so that the water-absorbing resin was dried sufficiently. An apparent density (unit: [g/cm$^3$]) of 5.00 g of the dried water-absorbing resin was measured by use of an automatic dry densimeter (AccuPycII 1340TC-10CC, manufactured by Shimadzu Corporation, carrier gas: helium). The measurement was repeated until five or more identical measured values were obtained consecutively.

(o-2) True Density

Internal gas bubbles (closed cells) present inside the water-absorbing resin have a diameter normally in a range of 1 μm to 300 μm. In pulverization, portions close to the closed cells are pulverized preferentially. Thus, when the water-absorbing resin is pulverized until a particle diameter thereof is less than 45 μm, the water-absorbing resin obtained after the pulverization has almost no closed cells. Therefore, in the present invention, a dried density of the water-absorbing resin having been pulverized until a particle diameter of the water-absorbing resin is less than 45 μm was specified as a true density. The measurement method is as follows. Specifically, 15.0 g of the water-absorbing resin and 400 g of columnar porcelain balls (diameter: 13 mm, length: 13 mm) were placed in a ball mill pot (available from TERAOKA, model No. 90, internal dimensions: 80 mm in diameter and 75 mm in height, external dimension: 90 mm in diameter and 110 mm in height), and then the ball mill pot was operated at 60 Hz for 2 hours, so that a water-absorbing resin which would pass through a JIS standard sieve having a mesh size of 45 μm (a water-absorbing resin whose particle diameter was less than 45 μm) was obtained. Then, 6.0 g of that water-absorbing resin whose particle diameter was less than 45 μm was dried at 180° C. for 3 hours or more as in "(0-1) Apparent density" described earlier, and thereafter the dried density was measured. The measurement value thus obtained was regarded as the "true density" of the present invention.

(o-3) Internal Gas Bubble Ratio

By use of an apparent density ($\rho 1$ [g/cm³]) measured by the method described earlier in "(o-1) Apparent density" and a true density ($\rho 2$ [g/cm³]) measured by the method described earlier in "(0-2) True density", an internal gas bubble ratio was defined by the following Formula:

Internal gas bubble ratio [%]={(true density [g/cm³]−apparent density [g/cm³])/true density [g/cm³]}×100

PRODUCTION EXAMPLES

As a device for producing a polyacrylic acid (salt)-based water-absorbing resin powder in the following Production Examples, there was prepared a continuous production device for carrying out a polymerization step, a gel-crushing step, a drying step, a pulverization step, a classification step, a surface-crosslinking step, a cooling step, a particle sizing step, and a transportation step for linking the above individual steps. The continuous production device had a production capacity of 3500 [kg/hr]. The above steps can each include a single line or two or more lines. In a case where the above steps include two or more lines, the production capacity is shown as the sum of the respective production amounts of the two or more lines. The continuous production device was used to continuously produce a polyacrylic acid (salt)-based water-absorbing resin powder.

Production Example 1

First, there was prepared an aqueous monomer solution (1) containing 300 parts by mass of acrylic acid, 100 parts by mass of a 48 mass % aqueous sodium hydroxide solution, 0.94 parts by mass of polyethylene glycol diacrylate (average n number: 9), 16.4 parts by mass of a 0.1 mass % aqueous trisodium diethylenetriamine pentaacetate solution, and 314.3 parts by mass of deionized water.

Next, the aqueous monomer solution (1) whose temperature had been adjusted to 38° C. was continuously fed by a metering pump, and then 150.6 parts by mass of a 48 mass % aqueous sodium hydroxide solution was further continuously line-mixed with the aqueous monomer solution (1). At this stage, the temperature of the aqueous monomer solution (1) was raised to 80° C. due to heat of neutralization.

Subsequently, 14.6 parts by mass of a 4 mass % aqueous sodium persulfate solution was continuously line-mixed with the aqueous monomer solution (1), and then a resultant mixture was continuously fed into a continuous polymerization device, having a planar polymerization belt with dams at both ends, so that the fed mixture had a thickness of 10 mm. Thereafter, polymerization (polymerization time: 3 minutes) was continuously carried out, so that a belt-shaped hydrogel (1) was obtained. The belt-shaped hydrogel (1) obtained was continuously cut at regular intervals in the width direction relative to the traveling direction of the polymerization belt so that the cut length was 300 mm. Thus, a hydrogel (1) was obtained. The hydrogel (1) had a CRC of 33.5 g/g and a resin solid content of 49.5 mass %.

Production Example 2

First, there was prepared an aqueous monomer solution (2) containing 300 parts by mass of acrylic acid, 100 parts by mass of a 48 mass % aqueous sodium hydroxide solution, 0.61 parts by mass of polyethylene glycol diacrylate (average n number: 9), 6.5 parts by mass of a 1.0 mass % aqueous pentasodium ethylenediamine tetra(methylene phosphonate) solution, and 346.1 parts by mass of deionized water.

Next, the aqueous monomer solution (2) whose temperature had been adjusted to 40° C. was continuously fed by a metering pump, and then 150.6 parts by mass of a 48 mass % aqueous sodium hydroxide solution was further continuously line-mixed with the aqueous monomer solution (2). At this stage, the temperature of the aqueous monomer solution (2) was raised to 81° C. due to heat of neutralization.

Subsequently, 14.6 parts by mass of a 4 mass % aqueous sodium persulfate solution was continuously line-mixed with the aqueous monomer solution (2), and then a resultant mixture was continuously fed into a continuous polymerization device, having a planar polymerization belt with dams at both ends, so that the fed mixture had a thickness of 10 mm. Thereafter, polymerization (polymerization time: 3 minutes) was continuously carried out, so that a belt-shaped hydrogel (2) was obtained. The belt-shaped hydrogel (2) obtained was continuously cut at regular intervals in the width direction relative to the traveling direction of the polymerization belt so that the cut length was 300 mm. Thus, a hydrogel (2) was obtained. The hydrogel (2) had a CRC of 36.0 g/g and a resin solid content of 48.1 mass %.

Production Example 3

First, there was prepared an aqueous monomer solution (3) containing 300 parts by mass of acrylic acid, 100 parts by mass of a 48 mass % aqueous sodium hydroxide solution, 1.46 parts by mass of polyethylene glycol diacrylate (average n number: 9), 16.4 parts by mass of a 0.1 mass % aqueous trisodium diethylenetriamine pentaacetate solution, and 361 parts by mass of deionized water.

Next, the aqueous monomer solution (3) whose temperature had been adjusted to 42° C. was continuously fed by a metering pump, and then 150.6 parts by mass of a 48 mass % aqueous sodium hydroxide solution was further continuously line-mixed with the aqueous monomer solution (3). At this stage, the temperature of the aqueous monomer solution (3) was raised to 81° C. due to heat of neutralization.

Subsequently, 14.6 parts by mass of a 4 mass % aqueous sodium persulfate solution was continuously line-mixed with the aqueous monomer solution (3), and then a resultant mixture was continuously fed into a continuous polymerization device, having a planar polymerization belt with dams at both ends, so that the fed mixture had a thickness of 10 mm. Thereafter, polymerization (polymerization time: 3 minutes) was continuously carried out, so that a belt-shaped hydrogel (3) was obtained. The belt-shaped hydrogel (3) obtained was continuously cut at regular intervals in the width direction relative to the traveling direction of the polymerization belt so that the cut length was 300 mm. Thus, a hydrogel (3) was obtained. The hydrogel (3) had a CRC of 33.3 g/g and a resin solid content of 47.1 mass %.

Comparative Production Example 1

First, there was prepared an aqueous monomer solution (1) containing 300 parts by mass of acrylic acid, 100 parts by mass of a 48 mass % aqueous sodium hydroxide solution, 0.59 parts by mass of polyethylene glycol diacrylate (average n number: 9), 16.4 parts by mass of a 0.1 mass % aqueous trisodium diethylenetriamine pentaacetate solution, and 238.1 parts by mass of deionized water.

Next, the aqueous monomer solution (1) whose temperature had been adjusted to 38° C. was continuously fed by a metering pump, and then 149.3 parts by mass of a 48 mass % aqueous sodium hydroxide solution was further continuously line-mixed with the aqueous monomer solution (1). At this stage, the temperature of the aqueous monomer solution (1) was raised to 82° C. due to heat of neutralization.

Subsequently, 12.5 parts by mass of a 4 mass % aqueous sodium persulfate solution was continuously line-mixed with the aqueous monomer solution (1), and then a resultant mixture was continuously fed into a continuous polymerization device, having a planar polymerization belt with dams at both ends, so that the fed mixture had a thickness of 10 mm. Thereafter, polymerization (polymerization time: 3 minutes) was continuously carried out, so that a belt-shaped hydrogel (4) was obtained. The belt-shaped hydrogel (4) obtained was continuously cut at regular intervals in the width direction relative to the traveling direction of the polymerization belt so that the cut length was 300 mm. Thus, a hydrogel (4) was obtained. The hydrogel (4) had a CRC of 34.5 g/g and a resin solid content of 52.1 mass %.

Example 1

Gel-Crushing

The hydrogel (1), which had been obtained in Production Example 1, was fed to a screw extruder so as to be subjected to gel-crushing. As the screw extruder, a meat chopper including a porous plate and a screw shaft was used. The porous plate was provided at a tip of the meat chopper and had a diameter of 100 mm, a pore diameter of 9.5 mm, 40 pores, an aperture ratio of 36.1%, and a thickness of 10 mm, and the screw shaft had an outer diameter of 86 mm. While the screw shaft of the meat chopper was being rotated at 130 rpm, the hydrogel (1) was fed at 4640 [g/min], and at the same time, water vapor was fed at 83 [g/min]. In this case, gel-grinding energy (GGE) was 26.9 [J/g], and GGE (2) was 13.6 [J/g]. The hydrogel (1) which had not been subjected to the gel-crushing had a temperature of 80° C., and the temperature was raised to 85° C. in a crushed gel obtained after the gel-crushing, i.e., a particulate hydrogel (1).

The particulate hydrogel (1) obtained through the above gel-crushing step had a resin solid content of 49.1 mass %, a mass average particle diameter (D50) of 994 μm, and a logarithmic standard deviation (σξ) of a particle size distribution of 1.01.

(Drying)

Next, the particulate hydrogel (1) was dispersed onto a through-flow plate within 1 minute of the end of the gel-crushing (at this stage, the particulate hydrogel (1) had a temperature of 80° C.), and dried at 185° C. for 30 minutes, so that a dried polymer (1) was obtained. Hot air had an average air velocity of 1.0 [m/s] in the direction perpendicular to the traveling direction of the through-flow belt. The air velocity of the hot air was measured with use of Anemomaster 6162, which is a constant temperature thermal anemometer manufactured by Kanomax Japan Inc.

(Pulverization and Classification)

Subsequently, the total amount of a dried polymer (1) obtained through the above drying step was fed to a three-stage roll mill so as to be pulverized (subjected to a pulverizing step). Thereafter, the dried polymer thus pulverized was further classified with use of JIS standard sieves having respective mesh sizes of 425 μm and 300 μm. Thus, water-absorbing resin particles (1) having a non-uniformly pulverized shape were obtained. The water-absorbing resin particles (1) had a CRC of 39.7 g/g.

(Surface Treatment and Additive Addition)

Next, with 100 parts by mass of the water-absorbing resin particles (1), a (covalently bonding) surface-crosslinking agent solution containing 0.025 parts by mass of ethyleneglycoldiglycidyl ether, 0.4 parts by mass of ethylene carbonate, 0.6 parts by mass of propylene glycol, and 3.0 parts by mass of deionized water was uniformly mixed. Then, a resultant mixture was heat-treated at 190° C. for approximately 45 minutes so that resultant water-absorbing resin powder (1) would have a CRC of 33 g/g. Thereafter, the mixture was cooled, water-absorbing resin powder obtained through the above operations were subjected to the paint shaker test (described earlier), and damage equivalent to that caused during a production process was caused to the water-absorbing resin powder. Then, with 100 parts by mass of the water-absorbing resin powder, an aqueous solution containing 1 part by mass of water and 0.01 parts by mass of trisodium diethylenetriamine pentaacetate was uniformly mixed. A resultant mixture was dried at 60° C. for 1 hour and then passed through a JIS standard sieve having a mesh size of 425 μm. To the mixture, 0.4 parts by mass of silicon dioxide (product name: Aerosil 200, manufactured by Nippon Aerosil Co., Ltd.) was uniformly added. Thus, a particulate water-absorbing agent (1) was obtained. Table 1 shows physical properties of the particulate water-absorbing agent (1).

Example 2

Operations similar to those carried out in Example 1 were carried out with use of the hydrogel (2) obtained in Production Example 2. In this way, a particulate water-absorbing agent (2) was obtained. Table 1 shows physical properties of the particulate water-absorbing agent (2).

Example 3

(Gel-Crushing)

The hydrogel (3), which had been obtained in Production Example 3, was fed to a screw extruder so as to be subjected to gel-crushing. As the screw extruder, a meat chopper including a porous plate and a screw shaft was used. The porous plate was provided at a tip of the meat chopper and had a diameter of 100 mm, a pore diameter of 6.4 mm, 83 pores, an aperture ratio of 41.4%, and a thickness of 10 mm, and the screw shaft had an outer diameter of 86 mm. While the screw shaft of the meat chopper was being rotated at 130 rpm, the hydrogel (3) was fed at 4640 [g/min], and at the same time, water vapor was fed at 83 [g/min]. In this case, gel-grinding energy (GGE) was 29.5 [J/g], and GGE (2) was 15.7 [J/g]. The hydrogel (3) which had not been subjected to the gel-crushing had a temperature of 80° C., and the temperature was raised to 86° C. in a crushed gel obtained after the gel-crushing, i.e., a particulate hydrogel (3).

The particulate hydrogel (3) obtained through the above gel-crushing step had a resin solid content of 46.5 mass %, a mass average particle diameter (D50) of 360 μm, and a logarithmic standard deviation (σξ) of a particle size distribution of 0.99.

(Drying)

Next, the particulate hydrogel (3) was dispersed onto a through-flow plate within 1 minute of the end of the gel-crushing (at this stage, the particulate hydrogel (3) had a temperature of 80° C.), and dried at 185° C. for 30 minutes, so that a dried polymer (3) was obtained. Hot air had an average air velocity of 1.0 [m/s] in the direction perpendicular to the traveling direction of the through-flow belt. The air velocity of the hot air was measured with use of Anemomaster 6162, which is a constant temperature thermal anemometer manufactured by Kanomax Japan Inc.

(Pulverization and Classification)

Subsequently, the total amount of a dried polymer (3) obtained through the above drying step was fed to a three-stage roll mill so as to be pulverized (subjected to a pulverizing step). Thereafter, the dried polymer thus pulverized was further classified with use of JIS standard sieves having respective mesh sizes of 425 μm and 300 μm. Thus, water-absorbing resin particles (3) having a non-uniformly pulverized shape were obtained. The water-absorbing resin particles (2) had a CRC of 39.2 g/g.

(Surface Treatment and Additive Addition)

Next, with 100 parts by mass of the water-absorbing resin particles (3), a (covalently bonding) surface-crosslinking agent solution containing 0.025 parts by mass of ethyleneglycoldiglycidyl ether, 0.4 parts by mass of ethylene carbonate, 0.6 parts by mass of propylene glycol, and 3.0 parts by mass of deionized water was uniformly mixed. Then, a resultant mixture was heat-treated at 190° C. for approximately 35 minutes so that resultant water-absorbing resin powder (3) would have a CRC of 34 g/g. Thereafter, the mixture was cooled, water-absorbing resin powder obtained through the above operations were subjected to the paint shaker test (described earlier), and damage equivalent to that caused during a production process was caused to the water-absorbing resin powder. Then, with 100 parts by mass of the water-absorbing resin powder, an aqueous solution containing 1 part by mass of water and 0.01 parts by mass of trisodium diethylenetriamine pentaacetate was uniformly mixed. A resultant mixture was dried at 60° C. for 1 hour and then passed through a JIS standard sieve having a mesh size of 425 μm. To the mixture, 0.4 parts by mass of silicon dioxide (product name: Aerosil 200, manufactured by Nippon Aerosil Co., Ltd.) was uniformly added. Thus, a particulate water-absorbing agent (3) was obtained. Table 1 shows physical properties of the particulate water-absorbing agent (3).

Example 4

With 100 parts by mass of the water-absorbing resin particles (1) obtained in Example 1, a surface-crosslinking agent solution containing 0.030 parts by mass of ethyleneglycoldiglycidyl ether, 1.0 parts by mass of propylene glycol, and 3.0 parts by mass of deionized water was uniformly mixed. Then, a resultant mixture was heat-treated at 100° C. for 45 minutes. Thereafter, the mixture was cooled, water-absorbing resin particles obtained through the above operations were subjected to the paint shaker test (described earlier), and damage equivalent to that caused during a production process was caused to the water-absorbing resin particles. Then, with 100 parts by mass of the water-absorbing resin particles (1), an aqueous solution containing 1 part by mass of water and 0.01 parts by mass of trisodium diethylenetriamine pentaacetate was uniformly mixed. A resultant mixture was dried at 60° C. for 1 hour and then passed through a JIS standard sieve having a mesh size of 425 μm. To the mixture, 0.4 parts by mass of silicon dioxide (product name: Aerosil 200, manufactured by Nippon Aerosil Co., Ltd.) was uniformly added. Thus, a particulate water-absorbing agent (4) was obtained. Table 1 shows physical properties of the particulate water-absorbing agent (4).

Example 5

With 100 parts by mass of the water-absorbing resin particles (1) obtained in Example 1, a surface-crosslinking agent solution containing 0.045 parts by mass of ethyleneglycoldiglycidyl ether, 1.0 parts by mass of propylene glycol, and 3.0 parts by mass of deionized water was uniformly mixed. Then, a resultant mixture was heat-treated at 100° C. for 45 minutes. Thereafter, the mixture was cooled, water-absorbing resin particles obtained through the above operations were subjected to the paint shaker test (described earlier), and damage equivalent to that caused during a production process was caused to the water-absorbing resin particles. Then, with 100 parts by mass of the water-absorbing resin particles (1), an aqueous solution containing 1 part by mass of water and 0.01 parts by mass of trisodium diethylenetriamine pentaacetate was uniformly mixed. A resultant mixture was dried at 60° C. for 1 hour and then passed through a JIS standard sieve having a mesh size of 425 μm. To the mixture, 0.4 parts by mass of silicon dioxide (product name: Aerosil 200, manufactured by Nippon Aerosil Co., Ltd.) was uniformly added. Thus, a particulate water-absorbing agent (5) was obtained. Table 1 shows physical properties of the particulate water-absorbing agent (5).

Comparative Example 1

(Gel-Crushing)

The comparative hydrogel (1), which had been obtained in Comparative Production Example 1, was fed to a screw extruder so as to be subjected to gel-crushing. As the screw extruder, a meat chopper including a porous plate and a screw shaft was used. The porous plate was provided at a tip of the meat chopper and had a diameter of 100 mm, a pore diameter of 16 mm, 16 pores, an aperture ratio of 49.4%, and a thickness of 10 mm, and the screw shaft had an outer diameter of 86 mm. While the screw shaft of the meat chopper was being rotated at 100 rpm, the comparative hydrogel (1) was fed at 4640 [g/min], and at the same time, water vapor was fed at 83 [g/min]. In this case, gel-grinding energy (GGE) was 15.8 [J/g], and GGE (2) was 4.8 [J/g]. The comparative hydrogel (1) which had not been subjected to the gel-crushing had a temperature of 80° C., and the temperature was raised to 81° C. in a crushed gel obtained after the gel-crushing, i.e., a comparative particulate hydrogel (1).

The comparative particulate hydrogel (1) obtained through the above gel-crushing step had a resin solid content of 51.5 mass %, a mass average particle diameter (D50) of 2086 μm, and a logarithmic standard deviation (σζ) of a particle size distribution of 3.79.

(Drying)

Next, the comparative particulate hydrogel (1) was dispersed onto a through-flow plate within 1 minute of the end of the gel-crushing (at this stage, the comparative particulate hydrogel (1) had a temperature of 80° C.), and dried at 185° C. for 30 minutes, so that a dried polymer (4) was obtained. Hot air had an average air velocity of 1.0 [m/s] in the direction perpendicular to the traveling direction of the through-flow belt. The air velocity of the hot air was measured with use of Anemomaster 6162, which is a constant temperature thermal anemometer manufactured by Kanomax Japan Inc.

(Pulverization and Classification)

Subsequently, the total amount of a comparative dried polymer (1) obtained through the above drying step was fed to a three-stage roll mill so as to be pulverized (subjected to a pulverizing step). Thereafter, the dried polymer thus pulverized was further classified with use of JIS standard sieves having respective mesh sizes of 850 μm and 150 μm. Thus, comparative water-absorbing resin particles (1) having a non-uniformly pulverized shape were obtained. The comparative water-absorbing resin particles (1) had a CRC of 45.1 g/g.

(Surface Treatment and Additive Addition)

Next, with 100 parts by mass of the comparative water-absorbing resin particles (1), a (covalently bonding) surface-crosslinking agent solution containing 0.025 parts by mass of ethyleneglycoldiglycidyl ether, 0.4 parts by mass of ethylene carbonate, 0.6 parts by mass of propylene glycol, and 3.0 parts by mass of deionized water was uniformly mixed. Then, a resultant mixture was heat-treated at 190° C. for approximately 35 minutes so that resultant comparative water-absorbing resin powder (1) would have a CRC of 34 g/g. Thereafter, the mixture was cooled, water-absorbing resin powder obtained through the above operations were subjected to the paint shaker test (described earlier), and damage equivalent to that caused during a production process was caused to the water-absorbing resin powder. Then, with 100 parts by mass of the comparative water-absorbing resin powder, an aqueous solution containing 1 part by mass of water and 0.01 parts by mass of trisodium diethylenetriamine pentaacetate was uniformly mixed. A resultant mixture was dried at 60° C. for 1 hour and then passed through a JIS standard sieve having a mesh size of 850 μm. To the mixture, 0.3 parts by mass of silicon dioxide (product name: Aerosil 200, manufactured by Nippon Aerosil Co., Ltd.) was uniformly added. Thus, a comparative particulate water-absorbing agent (1) was obtained. Table 1 shows physical properties of the comparative particulate water-absorbing agent (1).

Example 1 of Measurement Method

Figure 2:
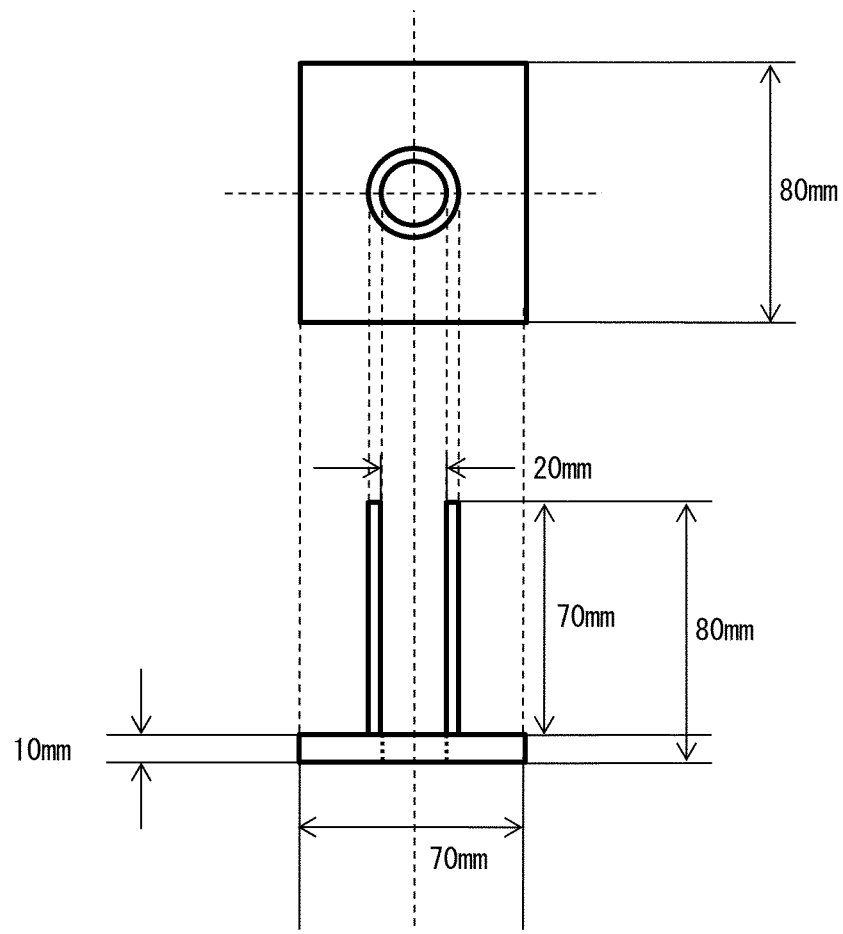
FIG. 2 is a plan view and a side view illustrating an example of a flat plate equipped with an injection inlet in the measurement device used in the measurement method according to the present invention.
Figure 3:
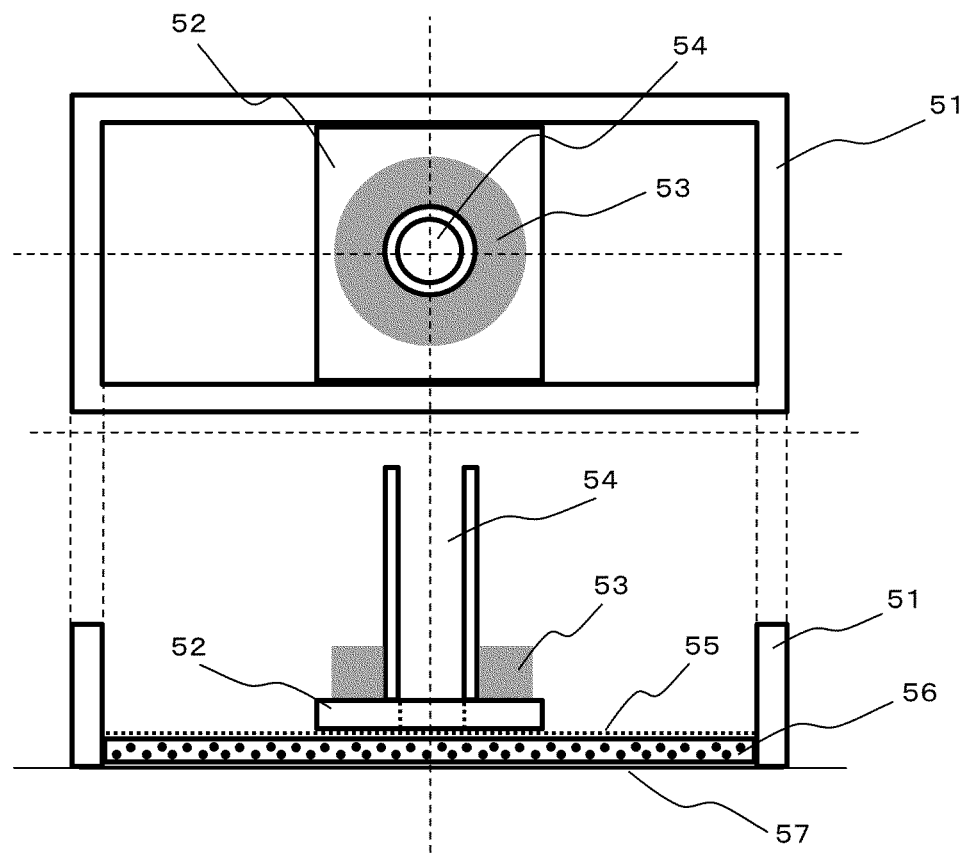
FIG. 3 is a plan view and a cross-sectional view schematically illustrating a measurement device used in the measurement method according to the present invention.

The following description will discuss Examples for measurements of absorption speed (absorption time) and re-wet by a method for measuring physical properties of a particulate water-absorbing agent of the present invention, with reference to FIGS. 1 to 3. The present invention is not limited only to the Examples, but can be appropriately changed according to the descriptions in the specification.

As illustrated in FIG. 3, a vinyl tape 57 (manufactured by Nitto Denko Corporation, Nitto vinyl tape No. 21-100™, 0.2 mm×100 mm×20 m, transparent) was attached to a bottom surface of a 3 cm high resin measurement container 51 having an opening of 8.1 cm long and 24.0 cm wide (see FIG. 1), so that the vinyl tape 57 had no wrinkle. A particulate water-absorbing agent 56 (3.84 g) was uniformly dispersed on the vinyl tape 57. Then, on the dispersed particulate water-absorbing agent 56 was placed a nonwoven fabric 55 (spunbonded nonwoven fabric having a mass per unit area of 18 g/m$^2$) cut to a size of 8 cm long and 24 cm wide.

Here, 10 sheets of 0.3 mm-thick spunbonded nonwoven fabric cut to a 8-cm square were layered on top of each other, clipped at their four corners, and immersed into a 0.9 mass % aqueous sodium chloride solution at 23° C. for 1 minute. Thereafter, from a mass increment after two-minute draining, a water absorption amount [g/m$^2$] per unit area of a single sheet of spunbonded nonwoven fabric was calculated as 213 [g/m$^2$]. In the present measurement method for calculating API and nAPI, a spunbonded nonwoven fabric having a water absorption amount of 190 to 230 [g/m$^2$] per unit area of a single sheet and a mass per unit area of 17.5 g/m$^2$ to 18.5 g/m$^2$ and having a thickness of 0.25 mm to 0.35 mm is used.

Then, a flat plate 52 measuring 8.0 cm long×7.0 cm wide and being detachably equipped with a cylindrical-shaped liquid injection inlet 54 having an inner diameter of 2.0 cm and a height of 7 cm (see FIG. 2) was placed in a central portion of the nonwoven fabric 55 such that the center of the measurement container 51 coincides with the liquid injection inlet 54. Further, on the flat plate 52 were placed weights 53 whose respective weights had been adjusted so that the weights would apply a load of 1.0 kPa (the weights 53 were placed so that the weights uniformly applied the pressure to the entire particulate water-absorbing agent).

In this state, 40 ml of a 0.9 mass % aqueous sodium chloride solution (liquid temperature: 37° C.) colored with 20 mg of blue No. 1 with respect to 1 L of the solution was introduced through the liquid injection inlet 54 (flow rate at the introduction of the solution was 8 ml/sec.) (first introduction). A time period from when the introduction of the solution was started to when the solution disappeared from the liquid injection inlet 54 was denoted as t1 (second). After it was observed that the solution had been taken in, the flat plate 52 was immediately removed. After an elapse of 10 minutes since the start of the first introduction of the solution, the flat plate 52 with the weight put thereon so that the same load as the load applied at the first introduction would be applied was placed again in the same manner as the first introduction. Subsequently, the second introduction of the solution was carried out. The amount of the solution was identical to that of the solution at the first introduction. Note that in a case where the solution did not disappear from the liquid injection inlet 54 even after the elapse of 10 minutes since the start of the first introduction of the solution, the solution was allowed to stand until the solution disappeared from the liquid injection inlet 54. Thereafter, the second introduction of the solution was immediately carried out. A time period from when the introduction of the solution was started to when the solution disappeared from the liquid injection inlet 54 was denoted as t2 (second). Subsequently, the same operation was carried out, and a time period from when a third introduction of the solution was started to when the solution disappeared from the liquid injection inlet 54 was denoted as t3 (second). After it was observed that the solution had been taken in, the liquid injection inlet 54 was immediately removed. After an elapse of 10 minutes since the start of the third introduction of the solution, 30 sheets of filter paper whose mass had been measured in advance (Each sheet was obtained by cutting a 100 mm×100 mm filter paper (manufactured by ADVANTEC, model No. 2) to a size of 8.0 cm long and 7.0 cm wide. The size of the filter paper can be changed if necessary.) were placed in the central portion of the nonwoven fabric 55. A weight serving as a load of 4.8 kPa was further placed on the 30 sheets of filter paper and was then held for 10 seconds. Note that in a case where the solution did not disappear from the liquid injection inlet 54 even after the elapse of 10 minutes since the start of the introduction of the solution, the solution was allowed to stand until the solution disappeared from the liquid injection inlet 54. Thereafter, the above operation was immediately carried out. After an elapse of 10 seconds, the weights 53 were removed, and the re-wet (g) was measured based on a mass increment of the filter paper.

(Absorbent Performance Index (API))

The absorption times (t1, t2, t3) and re-wet obtained by the above measurement method were used to determine the absorbent performance index (API) by the formula below.

t1: absorption time at first introduction (first absorption time) [sec]
t2: absorption time at second introduction (second absorption time) [sec]
t3: absorption time at third introduction (third absorption time) [sec]

Absorbent performance index (API)=$t1 \times t2 \times t3 \times$Re-wet [g]/1000=First absorption time [sec]$\times$Second absorption time [sec]$\times$Third absorption time [sec]$\times$Re-wet[g]/1000

(New Absorbent Performance Index (API))

The absorption times (t2, t3) and re-wet obtained by the above measurement method were used to determine the absorbent performance index (API) by the formula below.

t2: absorption time at second introduction (second absorption time) [sec]
t3: absorption time at third introduction (third absorption time) [sec]

New absorbent performance index (nAPI)=$t2 \times t3 \times$Re-wet [g]/10=Second absorption time [sec]$\times$Third absorption time [sec]$\times$Re-wet[g]/10

The absorbent performance index (API) and new absorbent performance index (nAPI) each indicate general absorbent performance of a particulate water-absorbing agent, represented by absorption times and rewet. Lower values of these indices indicate higher performance. The absorbent performance index (API) is preferably 150 or less, more preferably 125 or less, even more preferably 100 or less, particularly preferably 75 or less, and most preferably 50 or less. The new absorbent performance index (nAPI) is preferably 240 or less, more preferably 190 or less, even more preferably 150 or less, particularly preferably 130 or less, and most preferably 110 or less. By measuring the new absorbent performance index (nAPI), it is possible to evaluate the absorbent performance of a particulate water-absorbing agent more accurately.

The particulate water-absorbing agents (1) to (5) and the comparative particulate water-absorbing agent (1) were subjected to the measurements by the above methods. Table 2 shows the results of the measurements.

TABLE 1

| | CRC [g/g] | DAP10 min [g/g] | GPR [g/min] | Amount of water-absorbing resin contained in dust [ppm] | Surface tension [mN/m] | Index of DRC |
|---|---|---|---|---|---|---|
| Particulate water-absorbing agent (1) | 33 | 21 | 270 | 190 | 72 | 14.3 |
| Particulate water-absorbing agent (2) | 38 | 14 | 51 | 190 | 72 | 14.9 |
| Particulate water-absorbing agent (3) | 34 | 23 | 200 | 195 | 72 | 9.3 |
| Particulate water-absorbing agent (4) | 32 | 20 | 260 | 180 | 72 | 14.5 |
| Particulate water-absorbing agent (5) | 30 | 22 | 350 | 180 | 72 | 14.9 |
| Comparative particulate water-absorbing agent (1) | 34 | 23 | 116 | 190 | 72 | 43.9 |

TABLE 2

| | Absorption speed (absorption time) | | | | | | |
|---|---|---|---|---|---|---|---|
| | First absorption time t1 [sec] | Second absorption time t2 [sec] | Third absorption time t3 [sec] | Re-wet [g] | Absorbent performance index (API) | New absorbent performance index (nAPI) | Internal gas bubble ratio [%] |
| Particulate water-absorbing agent (1) | 44 | 24 | 17 | 2.5 | 45 | 102 | 1.8 |
| Particulate water-absorbing agent (2) | 65 | 38 | 34 | 1.1 | 92 | 142 | 1.8 |
| Particulate water-absorbing agent (3) | 40 | 20 | 16 | 3.2 | 41 | 102 | 1.8 |
| Particulate water-absorbing agent (4) | 43 | 23 | 17 | 2.7 | 45 | 106 | 1.7 |
| Particulate water-absorbing agent (5) | 47 | 21 | 16 | 3.7 | 58 | 124 | 1.7 |
| Comparative particulate water-absorbing agent (1) | 60 | 37 | 33 | 2.3 | 168 | 281 | 1.9 |

Example 1 of Absorbent Body

First, 35 g of the particulate water-absorbing agent (1) obtained in Example 1 and 15 g of wood-ground pulp were dry-mixed with use of a mixer. The resulting mixture was then spread out on a 400-mesh wire screen (with a mesh size of 38 μm), and was formed into a web (sheet) of paper with use of air in a batch-type air paper making device. The mixture formed into a sheet was then cut into a rectangular shape (with a size of 90 mm×330 mm) to be molded. Next, the molded mixture was pressed under a pressure of 196.14 kPa (2 [kgf/cm$^2$]) for 1 minute to prepare a child-disposable-diaper-size absorbent body (1).

The amount of particulate water-absorbing agent contained in the prepared absorbent body (1) was 5.9 g, the amount of pulp contained therein was 2.5 g, the concentration of the particulate water-absorbing agent in a core was approximately 70%, and the basis weight of the particulate water-absorbing agent was approximately 199 [g/m$^2$]. Next, the absorbent body, which is a mixture of pulp and a water-absorbing resin, of a Mamy Poko Pants Tappuri Kyushu Size M (purchased from Akachan Honpo, Himeji Hirohata store, Japan, in July 2018; number on the package upper surface: 201803053153) was taken out and then replaced by the absorbent body (1) wrapped with tissue paper. In this way, a pants-type absorbent article (1) was prepared.

Next, an infant doll (available from Koken Co., Ltd.; Infant Nursing Practice Model LM052; height: about 66 cm; weight: about 8 kg; material: silicone rubber) was fitted with the absorbent article (1). Further, as a liquid equivalent to urine was prepared a 0.90 mass % aqueous sodium chloride solution colored with 20 mg of Blue No. 1 per liter of the aqueous solution. Then, while the doll was laid with its face down on a flat plate, 60 ml of the aqueous sodium chloride solution (liquid temperature: 37° C.) was introduced three times at intervals of 10 minutes through a liquid-absorbing tube which was installed in an urination portion of the doll, so that the aqueous sodium chloride solution was absorbed into the absorbent body (1).

After the aqueous sodium chloride solution had been introduced, the absorbent article (1) was removed from the doll, and the state of the absorbent body (1) was observed. The state of the absorbent body (1) was evaluated in the following two items: diffusion property of the aqueous sodium chloride solution in the absorbent body (1); and dryness (state of re-wet) of an area corresponding to the urination portion. The evaluations were each made on a 1-to-5 scale below, and overall evaluation was made by multiplying two values of the respective evaluations (25 being best and 1 being worst). Table 3 shows the results.

5: Very good
4: Good
3: Average
2: Poor
1: Very poor

Examples 2 to 5 of Absorbent Bodies and Comparative Example 1

The same operation as in Example 1 of the absorbent body was carried out individually with use of the particulate water-absorbing agents (2) to (5) and the comparative particulate water-absorbing agent (1), and the state of the absorbent body (1) after the introduction of the aqueous sodium chloride solution was observed. Table 3 shows the results.

TABLE 3

| | Particulate water-absorbing agent used | Evaluation of diffusion property | Evaluation of dryness | Overall evaluation |
|---|---|---|---|---|
| Absorbent article (1) | Particulate water-absorbing agent (1) | 5 | 4 | 20 |
| Absorbent article (2) | Particulate water-absorbing agent (2) | 3 | 5 | 15 |
| Absorbent article (3) | Particulate water-absorbing agent (3) | 5 | 4 | 20 |
| Absorbent article (4) | Particulate water-absorbing agent (4) | 5 | 4 | 20 |
| Absorbent article (5) | Particulate water-absorbing agent (5) | 5 | 3 | 15 |
| Comparative absorbent article (1) | Comparative particulate water-absorbing agent (1) | 3 | 4 | 12 |

As is clear from the results in Tables 2 and 3, the absorbent bodies prepared with use of the particulate water-absorbing agents in accordance with the present invention which were excellent in absorbent performance index (API) and new absorbent performance index (nAPI) had an excellent balance between diffusion property and dryness even after having absorbed the aqueous sodium chloride solution a plurality of times and were thus evaluated highly. That is, the results in Tables 2 and 3 show that there is a correlation between absorbent performance index (API) and new absorbent performance index (nAPI), which are physical properties of the particulate water-absorbing agent, and diffusion property and dryness, which are physical properties of the absorbent body. This shows that physical property evaluations of an absorbent body enables physical property evaluation of a particulate water-absorbing agent.

INDUSTRIAL APPLICABILITY

The present invention allows physical properties required for a particulate water-absorbing agent to be measured by a method which is easier than the conventional measurement method. Further, the present invention can provide a particulate water-absorbing agent that has more excellent balance of fluid retention capacity, liquid permeability, and low dustiness and exhibits more excellent performance in an absorbent body than the conventional particulate water-absorbing agent. Further, the present invention can be used in various applications such as absorbent bodies for disposable diapers, sanitary napkins, and the like and absorbent articles using the absorbent bodies, sheets for pets, and waterproofing agents.

REFERENCE SIGNS LIST

1: Balance
2: Container
2a: Opening
2b: Opening
3: External air intake pipe
4: Duct
5: Measuring section
6: Glass filter
7: Filter paper
8: Sheet
9: Supporting cylinder
10: Metal gauze
11: Weight
12: 0.90 mass % aqueous sodium chloride solution
20: Plastic supporting cylinder 21: 400-mesh metal gauze made of stainless steel
22: Swollen gel
23: Petri dish
24: Glass filter
25: Filter paper
26: 0.90 mass % aqueous sodium chloride solution
31: Tank
32: Glass tube
33: 0.90 mass % aqueous sodium chloride solution
34: Cock-equipped L-shaped tube
35: Cock
40: container
41: Cell
42: Metal gauze made of stainless steel (mesh size of 38 μm)
43: Metal gauze made of stainless steel
44: Swollen gel
45: Metal gauze made of stainless steel (mesh size of 38 μm)
46: Piston
47: Holes
48: Collection container
49: Even balance
51: Measurement container
52: Flat plate
53: Weight
54: Liquid injection inlet
55: Non-woven fabric
56: Particulate water-absorbing agent
57: Vinyl tape

The invention claimed is:

1. A particulate water-absorbing agent having the following physical properties (1) and (2):
   (1) a centrifuge retention capacity (CRC) of 30 g/g to 50 g/g; and
   (2) a new absorbent performance index (nAPI) of 240 or less, the new absorbent performance index (nAPI) being expressed by the following formula:

New absorbent performance index (nAPI)=Second absorption time [sec]×Third absorption time [sec]×Re-wet [g]/10.

2. The particulate water-absorbing agent according to claim 1, wherein the new absorbent performance index (nAPI) is 190 or less.

3. The particulate water-absorbing agent according to claim 1, further having the following physical properties (3) to (5):
   (3) a value of diffusing absorbency under pressure after 10 minutes (DAP10 min) of 12.0 g/g or more;
   (4) a gel permeation rate (GPR) of 25 g/min or more; and
   (5) a content of a water-absorbing resin contained in a dust of said particulate water-absorbing agent of 300 ppm or less, with respect to the total amount of said particulate water-absorbing agent.

4. The particulate water-absorbing agent according to claim 1, wherein an index of DRC defined by the following Formula 1 is 43 or less, Index of DRC=(49−DRC5 min)/($D$50/1000)   Formula 1.

5. The particulate water-absorbing agent according to claim 4, wherein the index of DRC is 30 or less.

6. The particulate water-absorbing agent according to claim 1, wherein particles of said particulate water-absorbing agent have a non-uniformly pulverized particle shape.

7. The particulate water-absorbing agent according to claim 1, wherein a fluid retention capacity under pressure (AAP) is 18 g/g or more.

8. An absorbent body comprising a particulate water-absorbing agent according to claim 1.

9. An absorbent article comprising an absorbent body according to claim 8.

* * * * *